(12) United States Patent
De Fougerolles et al.

(10) Patent No.: US 7,972,597 B2
(45) Date of Patent: Jul. 5, 2011

(54) METHODS OF REDUCING CHEMOTAXIS USING ANTIBODIES AGAINST MONOCYTE CHEMOTACTIC PROTEINS

(75) Inventors: Antonin R. De Fougerolles, Brookline, MA (US); Victor E. Kotelianski, Boston, MA (US); Carl Reid, Mattapan, MA (US); Ellen Garber, Cambridge, MA (US)

(73) Assignee: Biogen Idec MA, Inc., Cambridge, MA (US)

( * ) Notice: Subject to any disclaimer, the term of this patent is extended or adjusted under 35 U.S.C. 154(b) by 0 days.

(21) Appl. No.: 12/612,087

(22) Filed: Nov. 4, 2009

(65) Prior Publication Data

US 2010/0166757 A1    Jul. 1, 2010

Related U.S. Application Data

(60) Division of application No. 12/171,791, filed on Jul. 11, 2008, now Pat. No. 7,632,501, which is a division of application No. 10/855,013, filed on May 27, 2004, now Pat. No. 7,405,277, which is a continuation of application No. PCT/US02/38229, filed on Nov. 27, 2002.

(60) Provisional application No. 60/343,391, filed on Nov. 30, 2001, provisional application No. 60/383,277, filed on May 24, 2002, provisional application No. 60/400,469, filed on Aug. 1, 2002.

(51) Int. Cl.
*A61K 39/395* (2006.01)

(52) U.S. Cl. ............... 424/130.1; 424/141.1; 424/145.1

(58) Field of Classification Search .................... None
See application file for complete search history.

(56) References Cited

U.S. PATENT DOCUMENTS 6,084,075 A    7/2000 Lind et al.
2007/0134236 A1    6/2007 De Fougerolles et al.

FOREIGN PATENT DOCUMENTS

| JP | 09067399 A | 3/1997 |
| WO | WO 95/09232 | 4/1995 |
| WO | WO-97/31949 | 9/1997 |
| WO | WO-00/05265 | 2/2000 |
| WO | WO-01/57226 A1 | 8/2001 |

OTHER PUBLICATIONS

Beers and Berkow. (1999). The Merck Manual of Diagnosis and Therapy, 17 th edition, pp. 1474-1476.*
Jee, Youngheun et al., "Upregulation of monocyte chemomatic protein-1 and CC chemokine receptor 2 in the central nervous system is closely associated with relapse of autoimmune encephalomyelitis in Lewis rats," *Journal of Neuroimmunology*, 128 (2002) 49-57.

Van Coillie et al. "The MCP/eotaxin Subfamily of CC Chemokines" *Cytokine & Growth Factor Reviews*, 10: 61-86 (1999).
Anonymous: "Antibodies to Cytokines & Cytokine Receptors," Downloaded from the internet Mar. 12, 2007, according to the European Patent Office.
Boring et al. "Decreased Lesion formation in CCR2-/-Mice Reveals a Role for Chemokines in the Initiation of Atherosclerosis." *Nature* 394(6696): 894-897 (1998).
Callard and Gearing (1994) The Cytokine Factsbook, Academic Pres Limited, pp. 171-173.
Campbell et al. "Monocyte Chemoattractant Protein 1 Mediates Cockroach Allergen-Induced Bronchial Hyperreactivity in Normal but not CCR2-/-Mice: the Role of Mast Cells." *The Journal of Immunology*, 163(4): 2160-2167 (1999).
Dean, "Preparation and Characterization of Monoclonal Antibodies to Proteins and Other Cellular Components," *Methods in Molecular Biology*, vol. 32: *Basic Protein and Peptide Protocols* (1994).
European Supplemental Search Report of Application No. EP 03 79 0088, mailed on May 3, 2006.
European Supplemental Search Report of Application No. EP 02 792 310.1, dated Dec. 20, 2007.
Huang et al. "Absence of Monocyte Chemoattractant Protein 1 in Mice Leads to Decreased Local Macrophage Recruitment and Antigen-Specific T Helper Cell Type 1 Immune Response in Experimental Autoimmune Encephalomyelitis" *Journal of Experimental Medicine*, 193(6): 713-725 (2001).
International Search Report of International Application No. PCT/US02/38229, mailed on Jul. 11, 2003.
International Search Report of International Application No. PCT/US03/37834, mailed on Jul. 23, 2004.
Lummus et al. "Diisocyanate Antigen-enhanced Production of Monocyte Chemoattractant Protein-1, IL-8, and Tumor Necrosis Factor-a by Peripheral Mononuclear Cells of Workers with Occupational Asthma," *Journal of Allergy and Clinic Immunology*, vol. 102(2):265-274, Aug. 1998.
Luo et al. "Serologic Analysis of the Mouse Beta Chemokine JE/Monocyte Chemoattractant Protein-1" *Journal of Immunology*, 153(8): 3708-3716 (1994).
Proost et al. "Human Monocyte Chemotactic Proteins 2 and 3: Structural and Functional Comparison with MCP-1." *Journal of Leukocyte Biology*, 59(1): 67-74 (1996).
Salcedo et al. "Human Endothelial Cells Express CCR2 and respond to MCP-1: Direct Role of MCP-1 in Angiogenesis and Tumor Progression." *Blood*, 96(1): 34-40 (2000).
Sawyer et al. "Methodology for Selection of Human Antibodies to Membrane Proteins from a Phage-Display Library," *Journal of Immunological Methods* 204:193-203 (1997).
Van Collie et al. "The MCP/eotaxin Subfamily of CC Chemokines" *Cytokine & Growth Factor Reviews*, 10:61-86 (1999).
Weber et al. "Expression of CCR2 by Endothelial Cells: Implications for MCP-1 Mediated Wound Injury Repair and in Vivo Inflammatory Activation of Endothelium." *Arteriosclerosis Thrombosis and Vascular Biology*, 19: 2085-2093 (1999).

\* cited by examiner

*Primary Examiner* — Prema Mertz
(74) *Attorney, Agent, or Firm* — Finnegan, Henderson, Farabow, Garrett & Dunner, LLP

(57) ABSTRACT

The invention provides antibodies that bind to a plurality of β-chemokines, particularly monocyte chemotactic proteins MCP-1, MCP-2 and MCP-3. The invention also provides cells producing the antibodies, and methods of making and using the same.

1 Claim, 11 Drawing Sheets

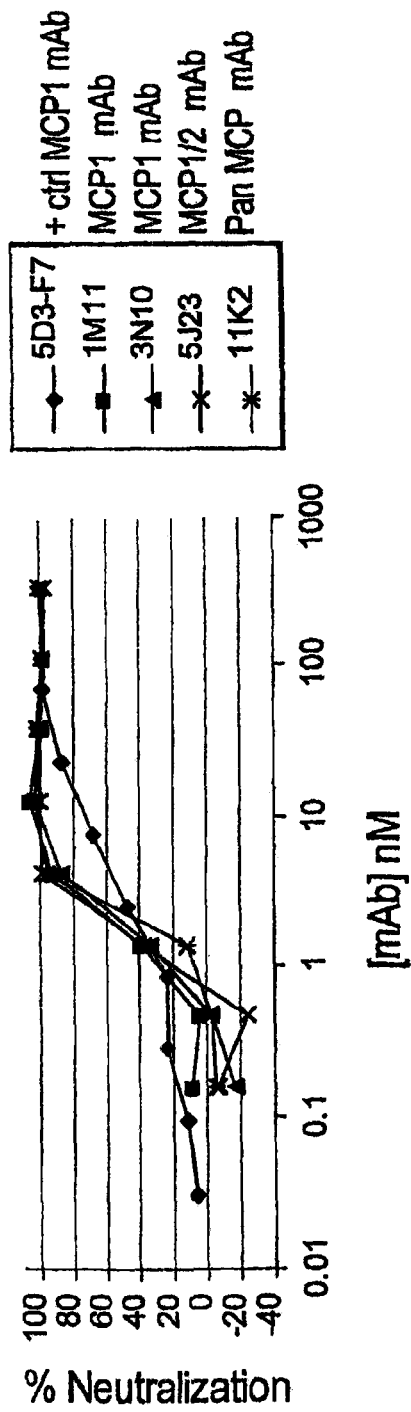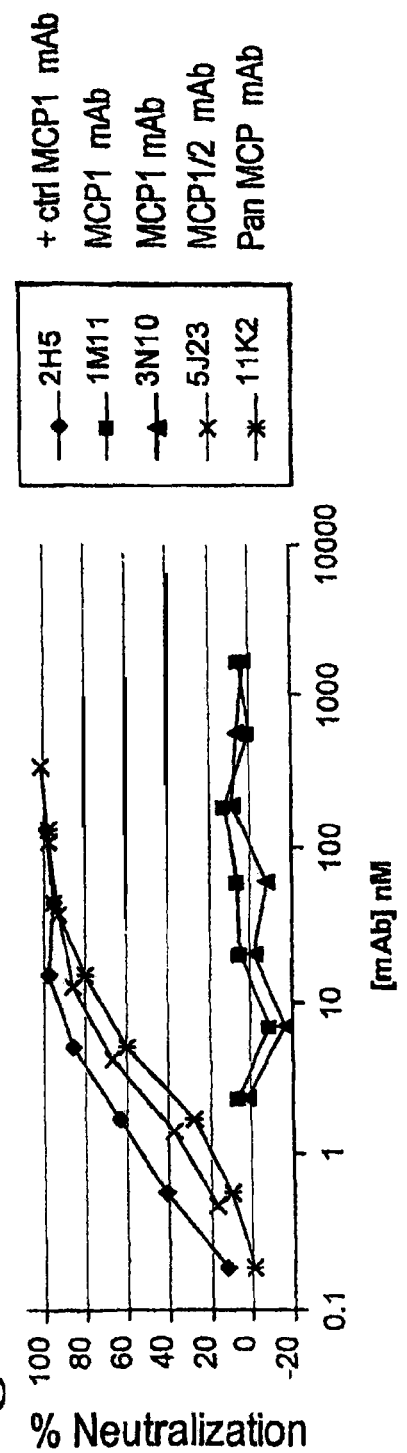

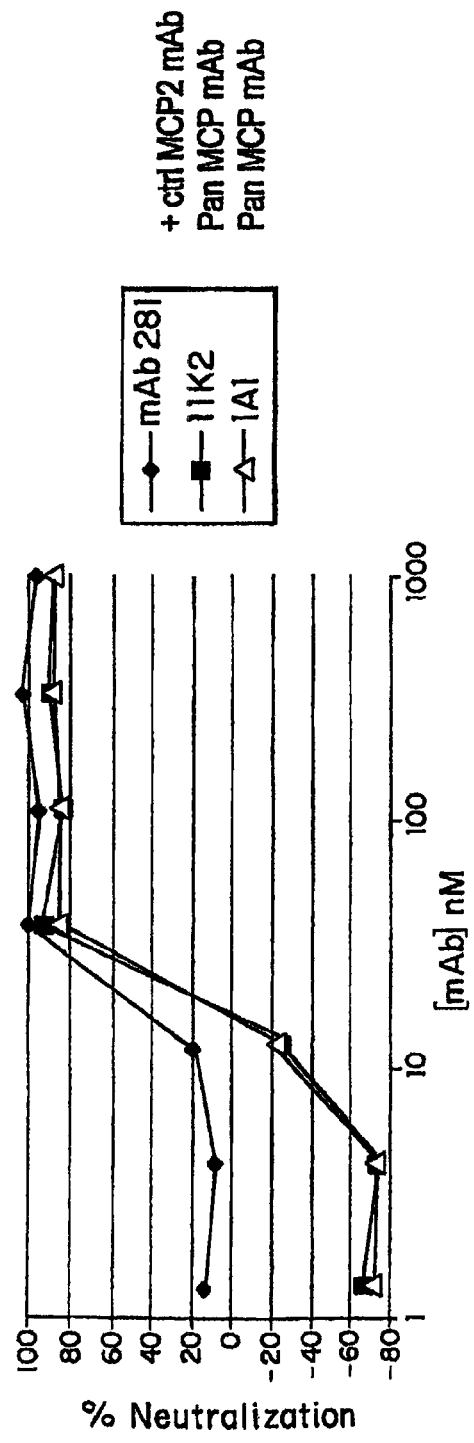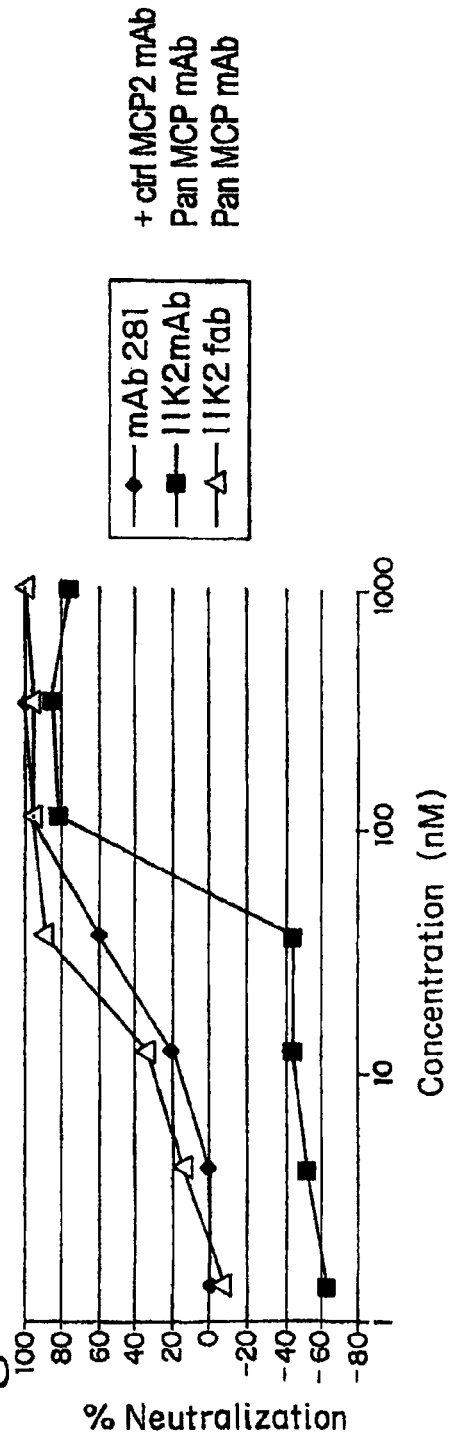

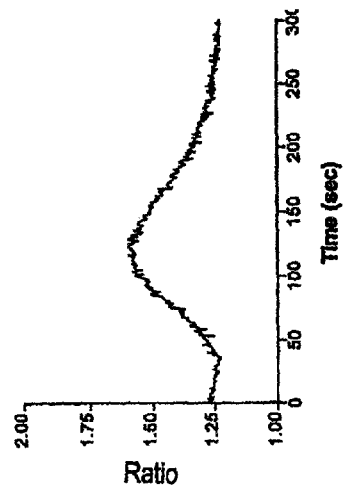
Fig. 7A  55.5 nM MCP-2
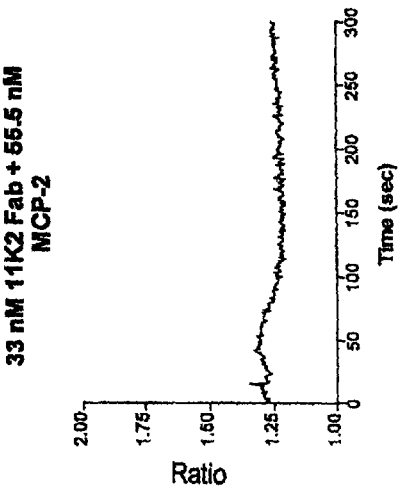
Fig. 7B  16.5 nM 11K2 mAb + 55.5 nM MCP-2
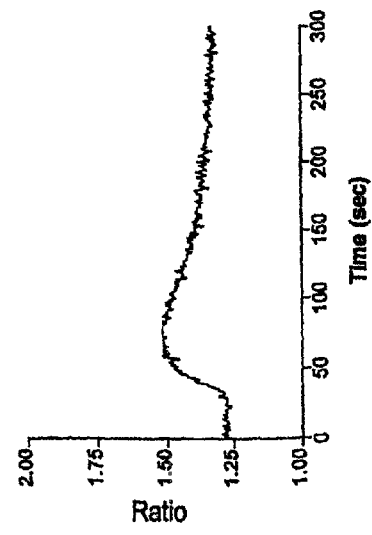
Fig. 7C  16.5 nM 11K2 F(ab')2 + 55.5 nM MCP-2
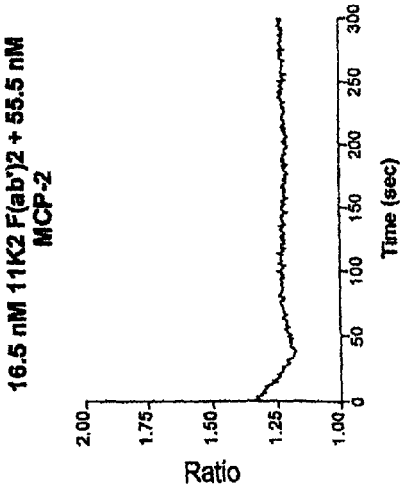
Fig. 7D  33 nM 11K2 Fab + 55.5 nM MCP-2

A. 1A1 Heavy Chain Variable Region

```
  1 GAGGTCCAGCTGCAGCAGTCTGGGGCAGAACTTGTGAGGTCAGGGGCCTCAGTCAAGTTG  60
    E  V  Q  L  Q  Q  S  G  A  E  L  V  R  S  G  A  S  V  K  L

CDR1
 61 TCCTGCACAGCTTCTGGCTTCAACATTAAAGACAACTATATGCACTGGGTGAAGCAGAGG 120
    S  C  T  A  S  G  F  N  I  K  D  N  Y  M  H  W  V  K  Q  R

CDR2
121 CCTGAACAGGGCCTGGAGTGGATTGGATGGATTGATCCTGAGAATGGAGATACTGAATAT 180
    P  E  Q  G  L  E  W  I  G  W  I  D  P  E  N  G  D  T  E  Y

181 GCCCCGAAGTTCCAGGGCAAGGCCACTATGACTGCAGACACATCCTCCAACACAGCCTAC 240
    A  P  K  F  Q  G  K  A  T  M  T  A  D  T  S  S  N  T  A  Y

CDR3
241 CTGCAGCTCAGCAGCCTGACATCTGAGGACACTGCCGTCTATTACTGTAATACATGGGCT 300
    L  Q  L  S  S  L  T  S  E  D  T  A  V  Y  Y  C  N  T  W  A

301 TACTACGGTACTAGCTACGGGGGATTTGCTTACTGGGGCCAAGGGACCACGGTCACCGTC 360
    Y  Y  G  T  S  Y  G  G  F  A  Y  W  G  Q  G  T  T  V  T  V

361 TCCTCA 366    (SEQ ID NO: 9)
    S  S          (SEQ ID NO: 11)
```

Fig. 8

B. 1A1 Light Chain Variable Region

```
  1 GATATCCAGATGACTCAGACTCCACTCACTTTGTCGGTTACCATTGGACAACCAGCCTCC 60
    D   I   Q   M   T   Q   T   P   L   T   L   S   V   T   I   G   Q   P   A   S

CDR1
 61 ATCTCTTGCAAGTCAAGTCAGAGCCTCTTAGATAGTGATGGAAAGACATATTTGAATTGG 120
    I   S   C   K   S   S   Q   S   L   L   D   S   D   G   K   T   Y   L   N   W

CDR2
121 TCGTTACAGAGGCCAGGCCAGTCTCCAAAGCGCCTAATCTATCTGGTGTCTAAACTGGAC 180
    S   L   Q   R   P   G   Q   S   P   K   R   L   I   Y   L   V   S   K   L   D

181 TCTGGAGTCCCTGACAGGTTCACTGGCAGTGGATCAGGGACAGATTTCACACTGAAAATC 240
    S   G   V   P   D   R   F   T   G   S   G   S   G   T   D   F   T   L   K   I

CDR3
241 AGCAGAGTGGAGGCTGAGGATTTGGGAGTTTATTATTGCTGGCAAGGTACACATTTTCCT 300
    S   R   V   E   A   E   D   L   G   V   Y   Y   C   W   Q   G   T   H   F   P

301 CAGACGTTCGGTGGAGGCACCAAGCTGGAGATCAAA 336     (SEQ ID NO: 10)
    Q   T   F   G   G   G   T   K   L   E   I   K          (SEQ ID NO: 12)
```

*Fig. 8*
(Continued)

A. 11K2 Heavy Chain Variable Region

```
  1 GAGGTTCAGCTGCAGCAGTCTGGGGCAGAGCTTGTGAAGGCAGGGGCCTCAGTCAAGTTG  60
    E  V  Q  L  Q  Q  S  G  A  E  L  V  K  A  G  A  S  V  K  L

CDR1
 61 TCCTGCCCAGCTTCTGGCCTCAACATTAAAGACACCTATATGCACTGGGTGAAGCAGAGG 120
    S  C  P  A  S  G  L  N  I  K  D  T  Y  M  H  W  V  K  Q  R

CDR2
121 CCTGAACAGGGCCTGGAGTGGATTGGAAGGATTGATCCTGCGAATGGTAATACTAAATTT 180
    P  E  Q  G  L  E  W  I  G  R  I  D  P  A  N  G  N  T  K  F

181 GACCCGAAGTTCCAGGGCAAGGCCACTATAACAGCAGACACATCCTCCAACACAGCCTAC 240
    D  P  K  F  Q  G  K  A  T  I  T  A  D  T  S  S  N  T  A  Y

CDR3
241 CTGCAGCTCAGCAGCCTGACATCTGAGGACACTGCCGTCTATTACTGTGCTAGAGGCGTC 300
    L  Q  L  S  S  L  T  S  E  D  T  A  V  Y  Y  C  A  R  G  V

301 TTTGGCTTTTTTGACTACTGGGGCCAAGGCACCACTCTCACAGTCTCCTCA 351 (SEQ ID NO: 25)
    F  G  F  F  D  Y  W  G  Q  G  T  T  L  T  V  S  S       (SEQ ID NO: 27)
```

*Fig.9*

B. 11K2 Light Chain Variable Region

```
  1 GACATTCAGATGACTCAGTCTTCATCCTCCTTTTCTGTATCTCTAGGAGACAGAGTCACC 60
    D  I  Q  M  T  Q  S  S  S  F  S  V  S  L  G  D  R  V  T

CDR1
 61 ATTACTTGCAAGGCAACTGAGGACATATATAATCGATTAGCCTGGTATCAGCAGAAACCA 120
    I  T  C  K  A  T  E  D  I  Y  N  R  L  A  W  Y  Q  Q  K  P

CDR2
121 GGAAGTGCTCCTAGGCTCTTAATTTCTGGTGCAACCAGTTTGGAGACTGGGGTTCCTTCA 180
    G  S  A  P  R  L  L  I  S  G  A  T  S  L  E  T  G  V  P  S

181 AGATTCAGTGGCAGTGGATCTGGAAAAGATTACACTCTCAGCATTACCAGTCTTCAGACT 240
    R  F  S  G  S  G  S  G  K  D  Y  T  L  S  I  T  S  L  Q  T

CDR3
241 GAGGATGTTGCTACTTATTACTGTCAACAGTTTTGGAGTGCTCCGTACACGTTCGGAGGG 300
    E  D  V  A  T  Y  Y  C  Q  Q  F  W  S  A  P  Y  T  F  G  G

301 GGGACCAAGCTGGAGATCAAA 321  (SEQ ID NO: 26)
    G  T  K  L  E  I  K        (SEQ ID NO: 28)
```

METHODS OF REDUCING CHEMOTAXIS USING ANTIBODIES AGAINST MONOCYTE CHEMOTACTIC PROTEINS

RELATED APPLICATIONS

This is a division of U.S. patent application Ser. No. 12/171,791, filed Jul. 11, 2008 now U.S. Pat. No. 7,632,501, which is a division of U.S. patent application Ser. No. 10/855,013, filed May 27, 2004 (issued as U.S. Pat. No. 7,405,277 on Jul. 29, 2008), which is a continuation of International Patent Application PCT/US02/038229 filed Nov. 27, 2002, which claims priority to U.S. Provisional Application No. 60/343,391, filed Nov. 30, 2001; 60/383,277, filed May 24, 2002; and 60/400,469, filed Aug. 1, 2002, all of which are incorporated herein by reference.

BACKGROUND OF THE INVENTION

The invention relates to antibodies that specifically recognize β-chemokines. Specifically, the invention is drawn to antibodies that specifically recognize monocyte chemotactic proteins designated MCP-1, MCP-2 and MCP-3, particularly antibodies that specifically bind to MCP-1 and MCP-2; MCP-2 and MCP-3, MCP-1 and MCP-3; and MCP-1, MCP-2 and MCP-3.

"Chemokines," which take their name from chemotactic cytokines, are small secreted polypeptides that regulate movement of immune cells into tissues (Baggiolini et of (1994) *Adv. Immunol.* 55:97-179; Oppenheim et al. (1991) *Ann Rev. Immunol.* 9:617-648). Chemokines are assigned to three different families based on the number and position of conserved cysteine residues (Van Calle et al. (1999) *Cytokine & Growth Factor Rev.* 10:61-86). The α and β chemokines each contain four conserved cysteine residues. The first two cysteines of the α chemokines are separated by a single amino acid, thus containing a CXC amino acid motif. The first two conserved cysteines of the β chemokines are adjacent. Thus, the β chemokines are also known as C-C chemokines. By contrast, lymphotactin is the sole member of the third family of chemokines, and contains only the second and fourth conserved cysteine residues. Interestingly, in humans, a chemokines are all encoded by genes on chromosome 4, β chemokines are all encoded by genes on chromosome 17, and lymphotaxin is encoded by genes on chromosome 1.

The β-chemokines form a gradient that serves as a chemoattractant and potential proliferation signal for immune and other cells such as monocytes, macrophages, basophils, eosinophils, T lymphocytes and fibroblasts. MCP-1, MCP-2 and MCP-3 share sequence homology with one another at the amino acid level. Through interaction with specific receptors, termed C-C chemokine receptors (CCR) which are G-protein coupled, seven transmembrane receptors (Rossi and Zlotnik (2000) *Ann. Rev. Immunol.* 18:217-242), the β-chemokines regulate the expression of adhesion molecules on endothelial cells and thereby indirectly affect diapedesis and extravasation of immune cells from the circulation into tissues. There are ten different CCRs (CCR1 through CCR10). CCR2 acts as a receptor for MCP-1, MCP-2, MCP-3, and MCP-4 (Rossi and Zlotnik (2000) *Ann. Rev. Immunol.* 18:217-242). However, all human MCPs have been shown to interact with more than one receptor (Van Coillie et al. (1999) *Cytokine & Growth Factor Rev.* 10:61-86).

Human MCP-1, MCP-2 and MCP-3 all have chemotactic activity for a variety of cell types, including T lymphocytes and monocytes (Van Coillie et al. (1999) *Cytokine & Growth Factor Rev.* 10:61-86). Other shared functions of MCP-1, MCP-2, and MCP-3 include induction of N-acetyl β-D-glucosaminidase release, gelatinase B release, and granzyme A release which are believed to help the cells digest the extracellular matrix components necessary to enable them to migrate into tissues (Van Coillie et al. (1999) *Cytokine & Growth Factor Rev.* 10:61-86). In addition, MCP-1 and MCP-3 share various functions, such as induction of arachidonic acid release and stimulation of a respiratory burst (Van Coillie et al. (1999) *Cytokine & Growth Factor Rev.* 10:61-86).

MCP-1-specific antibodies have previously been described in the literature (WO 01/89582, WO 01/89565, Luo et al. (1994) *J Immunol* 153:3708-16; Traynor, et at (2002) *J Immunol* 168:4659-66). Certain MCP-1 antibodies have been described as binding MCP-1 and MCP-3, specifically the MRHAS domain of MCP-1 and MCP-3 (WO 95/09232). In addition, a human anti-MCP-1 antibody has also been described (WO 02/02640). There is a need in the art to identify antibodies which can be used to manipulate β-chemokines in general, and to specifically modulate the activity of multiple chemokines, e.g., MCP-1 and MCP-2 or MCP-3.

SUMMARY OF THE INVENTION

The invention provides antibodies that specifically bind to a variety of β-chemokines, and monocyte chemotactic proteins in particular. The invention encompasses antibodies against individual β-chemokines and against β-chemokines in general. The so-called "pan-antibodies" of the invention bind to more than one of the β-chemokines, i.e., monocyte chemotactic proteins, MCP-1, MCP-2, and MCP-3.

The invention further provides antibodies that specifically bind to both MCP-1 and MCP-2, both MCP-2 and MCP-3, both MCP-1 and MCP-3 (to a region other than an MCP MRHAS motif), or to all three of MCP-1, MCP-2 and MCP-3.

In some embodiments, the antibodies are monoclonal antibodies. The monoclonal antibodies of the invention are preferably mammalian antibodies. In some embodiments, the antibodies are human antibodies.

In some embodiments, the antibodies are selected from the group consisting of 11K2.1 (ATCC Accession No. PTA-3987), 6D21.1 (ATCC Accession No. PTA-3989), 4N4.1 (ATCC Accession No. PTA-3994), 5A13.1 (ATCC Accession No. PTA-3995), 7H1.1 (ATCC Accession No. PTA-3985), 1A1.1 (ATCC Accession No. PTA-3990), 6I5.1 (ATCC Accession No. PTA-3986), 2O24.1 (ATCC Accession No. PTA-3993), 9B11.1 (ATCC Accession No. PTA-3992), 9B12.1 (ATCC Accession No. PTA-3996), 9C11.1 (ATCC Accession No. PTA-3988), and 12F15.1 (ATCC Accession No. PTA-3991).

The invention further provides antibody fragments that specifically bind to a variety of β-chemokines, particularly monocyte chemotactic proteins, including both MCP-1 and MCP-2, both MCP-2 and MCP-3, both MCP-1 and MCP-3 (to a region other than an MCP MRHAS motif), or to all three of MCP-1, MCP-2 and MCP-3. The antibody fragments include Fab, Fab', F(ab')$_2$, and F$_v$. The invention also embraces single chain antibodies, chimeric antibodies and humanized antibodies.

In some embodiments, the antigen-binding fragments of the antibodies are antigen-binding fragments of antibodies selected from the group consisting of 11K2.1 (ATCC Accession No. PTA-3987), 6D21.1 (ATCC Accession No. PTA-3989), 4N4.1 (ATCC Accession No. PTA-3994), 5A13.1 (ATCC Accession No. PTA 3995), 7H1.1 (ATCC Accession No. PTA-3985), 1A1.1 (ATCC Accession No. PTA-3990), 6I5.1 (ATCC Accession No. PTA-3986), 2O24.1 (ATCC Accession No. PTA-3993), 9B11.1 (ATCC Accession No. PTA-3992), 9B12.1 (ATCC Accession No. PTA-3996), 9C11.1 (ATCC Accession No. PTA-3988), and 12F15.1 (ATCC Accession No. PTA-3991).

The invention further provides hybridoma and transformed cells producing any of the antibodies or antigen-binding fragments described herein.

In some embodiments, the antibodies and antigen-binding fragments thereof may be chemically modified to provide a desired effect. In some embodiments the antibodies or antigen-binding fragments thereof are conjugated to polyethylene glycol or albumen.

In some embodiments, the antibodies and antigen-binding fragments thereof may be conjugated to a toxins, or radioisotopes.

The invention further provides in vitro immunoassays for detecting β-chemokines in samples.

The invention also provides therapeutic compositions containing at least one of the anti-β-chemokine antibodies provided herein in a pharmaceutically acceptable carrier.

The invention also provides methods of producing the anti-β-chemokine antibodies and anti-β-chemokine antibody producing cells provided herein.

The invention also provides methods of inhibiting the activity of β-chemokines comprising administering to an animal a composition comprising a pharmaceutically acceptable carrier and an antibody that binds to at least one β-chemokine or antigen-binding fragment thereof. In some embodiments, the antibody binds MCP-1 and MCP-2. In other embodiments, the antibody binds MCP-2 and MCP-3. In other embodiments, the antibody binds MCP-1 and MCP-3 to a region other than an MRHAS motif. In other embodiments, the antibody binds MCP-1, MCP-2 and MCP-3.

The invention also provides methods of blocking chemotaxis comprising administering to an animal a composition comprising a pharmaceutically acceptable carrier and a antibody or antigen-binding fragment that binds to at least one β-chemokine. In some embodiments, the antibody binds MCP-1 and MCP-2. In other embodiments, the antibody binds MCP-2 and MCP-3. In other embodiments, the antibody binds MCP-1 and MCP-3 to a region other than an MRHAS motif. In other embodiments, the antibody binds MCP-1, MCP-2 and MCP-3.

The invention also provides methods of modulating β-chemokine activity in vitro and in vivo using the antibodies or antigen-binding fragments, and compositions provided herein. As such, the antibodies or antigen-binding fragments of the invention are useful in the treatment of diseases and disorders including, but not limited to: inflammatory conditions and pathological conditions associated with MCP.

In certain embodiments, the antibodies or antigen binding fragments thereof of the present invention are useful in the treatment of glomerulonephritis, scleroderma, cirrhosis, multiple sclerosis, lupus nephritis, atherosclerosis, rheumatoid arthritis, and inflammatory bowel disease.

The invention provides antibodies or antigen-binding fragments thereof, that bind to MCP-1, MCP-2 and/or MCP-3 wherein the antibodies, or antigen binding fragments thereof, have a Kd for binding to MCP-1, MCP-2 and/or MCP-3 of about 1 pM or less, about 0.7 pM or less or about 0.4 pM or less. The invention also provides antibodies or antigen-binding fragments thereof, that bind to MCP-1, MCP-2 and/or MCP-3 comprising a Fab fragment wherein the Fab fragment has a Kd for binding to MCP-1, MCP-2 and/or MCP-3 of about 15 pM or less, about 13 pM or less or about 11 pM or less.

The invention provides an antibody, or antigen-binding fragment thereof, comprising a variable heavy chain region as set forth in SEQ ID NO:11 and a variable light chain region as set forth in SEQ ID NO:12. In one embodiment, the antibody is a chimeric antibody. In another embodiment, the antibody is a humanized antibody. In still another embodiment, the antibody of the invention is a Fab fragment.

The invention also provides an isolated polypeptide comprising a fragment of SEQ ID NO:11 selected from the group consisting of amino acids 31-35 of SEQ ID NO:11, ammo acids 50-66 of SEQ ID NO:11, and amino acids 99-111 of SEQ ID NO:11. In another embodiment, the invention provides an isolated polypeptide comprising amino acids 31-35 of SEQ ID NO:11, amino acids 50-66 of SEQ ID NO:11 and amino acids 99-111 of SEQ ID NO:11. In a further embodiment, the invention provides an isolated polypeptide comprising the amino acid sequence of SEQ ID NO:11.

In another embodiment, the invention features an isolated polypeptide comprising a fragment of SEQ ID NO:12 selected from the group consisting of amino acids 24-39 of SEQ ID NO:12, amino acids 55-61 of in SEQ ID NO:12, and amino acids 94-102 of SEQ ID NO:12. The invention also features an isolated polypeptide comprising amino acids 24-39 of SEQ ID NO:12, amino acids 55-61 of SEQ ID NO:12, and amino acids 94-102 of SEQ ID NO:12. In yet another embodiment, the invention provides an isolated polypeptide comprising the amino acid sequence of SEQ ID NO:12.

In some embodiments, the invention provides a variant of a polypeptide comprising the amino acid sequence of SEQ ID NO:11, said variant comprising at least one conservative amino acid substitution, wherein the variant retains the ability to bind to MCP-1 with a Kd of about 0.7 pM or less. In another embodiment, the invention features a variant of a polypeptide comprising the amino acid sequence of SEQ ID NO:11, said variant comprising at least one conservative amino acid substitution, wherein the variant retains the ability to bind MCP-2 with a Kd of about 1.2 pM or less. In yet another embodiment, the invention provides a variant of a polypeptide comprising the amino acid sequence of SEQ ID NO:12, said variant comprising at least one conservative amino acid substitution, wherein the variant retains the ability to bind MCP-1 with a Kd of about 0.7 pM or less. In still another embodiment, the invention features a variant of a polypeptide comprising the amino acid sequence of SEQ ID NO:12, said variant comprising at least one conservative amino acid substitution, wherein the variant retains the ability to bind MCP-2 with a Kd of about 1.2 pM or less.

The invention provides an isolated polypeptide comprising the amino acid sequence of SEQ ID NO:11 and SEQ ID NO:12.

In one embodiment, the invention features an antibody heavy chain comprising a variable region complementarity determining region (CDR) from the 11K2 antibody heavy chain variable region set forth in SEQ ID NO:27. The invention also features an antibody light chain comprising a variable region complementarity determining region (CDR) from the 11K2 antibody light chain variable region set forth in SEQ ID NO:28. The invention provides an antibody, or antigen-binding fragment thereof, comprising a variable heavy chain region as set forth in SEQ ID NO:27 and a variable light chain region as set forth in SEQ ID NO:28. In one embodiment of the invention, the antibody is a chimeric antibody. In still another embodiment, the antibody of the invention is a humanized antibody. In still another embodiment, the antibody of the invention is a Fab fragment.

The invention provides an isolated polypeptide comprising a fragment of SEQ ID NO:27 selected from the group consisting of amino acids 31-35 of SEQ ID NO:27, amino acids 50-66 of SEQ ID NO:27, and amino acids 99-106 of SEQ ID NO:27.

The invention also features an isolated polypeptide comprising amino acids 31-35 of SEQ ID NO:27, amino acids 50-66 of SEQ ID NO:27, and amino acids 99-106 of SEQ ID NO:27. Still another feature of the invention is an isolated polypeptide comprising the amino acid sequence of SEQ ID NO:27.

In another embodiment, the invention provides an isolated polypeptide comprising a fragment of SEQ ID NO:28 selected from the group consisting of amino acids 24-34 of SEQ ID NO:28, amino acids 50-56 of in SEQ ID NO:28, and amino acids 89-97 of SEQ ID NO:28. The invention also provides an isolated polypeptide comprising amino acids 24-34 of in SEQ ID NO:28, amino acids 50-56 of SEQ ID NO:28, and amino acids 89-97 of SEQ ID NO:28. In still another embodiment, the invention provides an isolated polypeptide comprising the amino acid sequence of SEQ ID NO:28.

In some embodiments, the invention provides a variant of a polypeptide comprising the amino acid sequence of SEQ ID NO:27, said variant comprising at least one conservative amino acid substitution, wherein the variant retains the ability to bind MCP-1 with a Kd of about 0.4 pM or less. The invention also features a variant of a polypeptide comprising the amino acid sequence of SEQ ID NO:27, said variant comprising at least one conservative amino acid substitution, wherein the variant retains the ability to bind MCP-2 with a Kd of about 18 pM or less. In another embodiment, the invention features a variant of a polypeptide comprising the amino acid sequence of SEQ ID NO:28, said variant comprising at least one conservative amino acid substitution, wherein the variant retains the ability to bind MCP-1 with a Kd of about 0.4 pM or less. In still another embodiment, the invention provides a variant of a polypeptide comprising the amino acid sequence of SEQ ID NO:28, said variant comprising at least one conservative amino acid substitution, wherein the Variant retains the ability to bind MCP-2 with a Kd of about 18 pM or less.

The invention provides an isolated polypeptide comprising the amino acid sequence of SEQ ID NO:27 and SEQ ID NO:28.

The invention features an isolated nucleic acid encoding the immunoglobulin of SEQ ID NO:11, SEQ ID NO:12, SEQ ID NO:27, and SEQ ID NO:28. The invention also provides isolated nucleic acid molecules encoding the polypeptide of any one of SEQ ID NO:13, SEQ ID NO:14, SEQ ID NO:15, SEQ ID NO:16, SEQ ID NO:17, SEQ ID NO:18, SEQ ID NO:29, SEQ ID NO:30, SEQ ID NO:31, SEQ ID NO:32, SEQ ID NO:33, and SEQ ID NO:34. In another embodiment, the invention provides isolated nucleic acid molecules comprising SEQ ID NO:9, SEQ ID NO:10, SEQ ID NO: 25, and SEQ ID NO:26. In one embodiment, the invention features a vector comprising the nucleic acid molecules of the invention. In addition, the invention features a host cell comprising the nucleic acids of the invention. The invention also features a method of producing a antibody or fragment thereof, comprising culturing the host cell comprising the nucleic acids of the invention under conditions such that the antibody or fragment is produced and isolating said antibody from the host cell or culture.

The invention further provides an antibody heavy chain comprising variable region complementarity determining regions (CDRs) from the 1A1 antibody heavy chain variable region set forth as SEQ ID NO:11. The invention further provides an antibody light chain comprising variable region complementarity determining regions (CDRs) from the 1A1 antibody light chain variable region set forth as SEQ ID NO:12.

The invention further provides an antibody heavy chain comprising variable region complementarity determining regions (CDRs) from the 11K2 antibody heavy chain variable region set forth as SEQ ID NO:27. The invention also provides an antibody light chain comprising variable region complementarity determining regions (CDRs) from the 11K2 antibody light chain variable region set forth as SEQ ID NO:28.

The invention also features an isolated antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDRs: CDR1, CDR2, or CDR3, from the 1A1 heavy chain variable region set forth as SEQ ID NO:11. In another embodiment, the invention provides an isolated antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDR combinations: CDR1 and CDR2; CDR1 and CDR3; CDR2 and CDR3; and CDR1, CDR2, and CDR3, from the 1A1 heavy chain variable region set forth as SEQ ID NO:11.

The invention provides an isolated antibody, or antigen binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDRs: CDR1, CDR2, or CDR3, from the 1A1 light chain variable region set forth as SEQ ID NO:12. In another embodiment, the invention provides an isolated antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDR combinations: CDR1 and CDR2; CDR1 and CDR3; CDR2 and CDR3; or CDR1, CDR2, and CDR3, from the 1A1 light chain variable region set forth as SEQ ID NO:12.

The invention features an isolated antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDRs: CDR1, CDR2, or CDR3, from the 11K2 heavy chain variable region set forth as SEQ ID NO:27. In an additional embodiment, the invention features an isolated antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDR combinations: CDR1 and CDR2; CDR1 and CDR3; CDR2 and CDR3; or CDR1, CDR2, and CDR3, from the 11K2 heavy chain variable region set forth as SEQ ID NO:27.

The invention also provides an isolated antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDRs: CDR1, CDR2, or CDR3, from the 11K2 light chain variable region set forth as SEQ ID NO:28. In another embodiment, the invention provides an isolated antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment comprises at least one of the following CDR combinations: CDR1 and CDR2; CDR1 and CDR3; CDR2 and CDR3; or CDR1, CDR2, and CDR3, from the 11K2 light chain variable region set forth as SEQ ID NO:28.

The invention provides an antibody, or antigen-binding fragment thereof, which binds a plurality of β-chemokines, and wherein said chemokines comprise MCP-1 and at least one other β-chemokine (e.g., MCP-2), wherein said antibody or antigen-binding fragment thereof comprises a heavy chain variable region having a CDR1 domain comprising the sequence set forth as SEQ ID NO:13, a CDR2 domain comprising the sequence set forth as SEQ ID NO:14, and a CDR3 domain comprising the sequence set forth as SEQ ID NO:15. In one embodiment, the antibody of the invention is a chimeric antibody.

The invention also provides an antibody or antigen-binding fragment thereof, which binds a plurality of β-chemokines, and wherein said β-chemokines comprise MCP-1 and at least one other β-chemokine (e.g., MCP-2), wherein said antibody or antigen-binding fragment thereof comprises a light chain variable region having a CDR1 domain comprising the sequence set forth as SEQ ID NO:16, a CDR2 domain comprising the sequence set forth as SEQ ID NO:17, and a CDR3 domain comprising the sequence set forth as SEQ ID NO:18.

The invention further provides an antibody, or antigen-binding fragment thereof, which binds a plurality of β-chemokines, and wherein said β-chemokines comprise MCP-1 and at least one other β-chemokine (e.g., MCP-2), wherein said antibody or antigen-binding fragment thereof comprises a heavy chain variable region having a CDR1 domain comprising the sequence set forth as SEQ ID NO:13, a CDR2 domain comprising the sequence set forth as SEQ ID NO:14, and a CDR3 domain comprising the sequence set forth as SEQ ID NO:15, and a light chain variable region having a CDR1 domain comprising the sequence set forth as SEQ ID NO:16, a CDR2 domain comprising the sequence set forth as SEQ ID NO:17, and a CDR3 domain comprising the sequence set forth as SEQ ID NO:18.

The invention provides an antibody or antigen-binding fragment thereof, which binds a plurality of β-chemokines, and wherein said β-chemokines comprise MCP-1 and at least one other β-chemokine (e.g., MCP-2), wherein said antibody or antigen-binding fragment thereof comprises a heavy chain variable region having a CDR1 domain comprising the sequence set forth as SEQ ID NO:29, a CDR2 domain comprising the sequence set forth as SEQ ID NO:30, and a CDR3 domain comprising the sequence set forth as SEQ ID NO:31.

In addition, the invention provides an antibody, or antigen-binding fragment thereof, which binds a plurality of β-chemokines, wherein said β-chemokines comprise MCP-1 and at least one other β-chemokine (e.g., MCP-2), and wherein said antibody or antigen-binding fragment thereof comprises a light chain variable region having a CDR1 domain comprising the sequence set forth as SEQ ID NO:32, a CDR2 domain comprising the sequence set forth as SEQ ID NO:33, and a CDR3 domain comprising the sequence set forth as SEQ ID NO:34. In one embodiment, the antibody of the invention is a chimeric antibody. In another embodiment, the antibody of the invention is a humanized antibody.

The invention further provides an antibody or antigen-binding fragment thereof, which binds a plurality of β-chemokines, wherein said β-chemokines comprise MCP-1 and at least one other β-chemokine (e.g., MCP-2), and wherein said antibody or antigen-binding fragment thereof comprises a heavy chain variable region having a CDR1 domain comprising the sequence set forth as SEQ ID NO:29, a CDR2 domain comprising the sequence set forth as SEQ ID NO:30, and a CDR3 domain comprising the sequence set forth as SEQ ID NO:31, and a light chain variable region having a CDR1 domain comprising the sequence set forth as SEQ ID NO:32, a CDR2 domain comprising the sequence set forth as SEQ ID NO:33, and a CDR3 domain comprising the sequence set forth as SEQ ID NO:34. In one embodiment, the antibody of the invention is a chimeric antibody. In another embodiment, the antibody of the invention is a humanized antibody.

In one embodiment, the invention provides an isolated polypeptide encoding a CDR3 domain comprising an amino acid sequence selected from the group consisting of SEQ ID NO:15, SEQ ID NO:18, SEQ ID NO:31, and SEQ ID NO:34. In another embodiment, the invention features an isolated polypeptide encoding a CDR2 domain comprising an amino acid sequence selected from the group consisting of SEQ ID NO:14, SEQ ID NO:17, SEQ ID NO:30, and SEQ ID NO:33. In still another embodiment, the invention provides an isolated polypeptide encoding a CDR1 domain comprising an amino acid sequence selected from the group consisting of SEQ ID NO:13, SEQ ID NO:16, SEQ ID NO:29, and SEQ ID NO:32.

In yet another embodiment, the invention features an antibody heavy chain comprising a variable region complementarity determining region (CDR) from the 11K2 antibody heavy chain variable region set forth in SEQ ID NO:27. The invention also features an antibody light chain comprising a variable region complementarity determining region (CDR) from the 11K2 antibody light chain variable region set forth in SEQ ID NO:8. In still a further embodiment, the invention features an antibody or antigen-binding fragment thereof, comprising a variable heavy chain region as set forth in SEQ ID NO:27 and a variable light chain region as set forth in SEQ ID NO:28.

In another embodiment, the invention features an antibody, or antigen-binding fragment thereof, which binds a plurality of chemokines, wherein said β-chemokines comprise MCP-1 and at least one other β-chemokine, and wherein said antibody or antigen-binding fragment comprises the variable region complementarity determining region (CDR) from the 11K2 heavy chain variable region set forth in SEQ ID NO:27. The invention also features an antibody, or antigen-binding fragment thereof, which binds a plurality of chemokines, wherein said β-chemokines comprise MCP-1 and at least one other β-chemokine, and wherein said antibody or antigen-binding fragment comprises the variable region complementarity determining region (CDR) from the 11K2 light chain variable region set forth in SEQ ID NO:28. In yet another embodiment, at least one other β-chemokine is MCP-2.

Another embodiment of the invention includes an antibody, or antigen-binding fragment thereof, which binds a plurality of β-chemokines, wherein said β-chemokines comprise MCP-1 and at least one other β-chemokine, and wherein said antibody or antigen-binding fragment comprises a heavy chain variable region having a CDR1 domain comprising the sequence set forth in SEQ ID NO:29, a CDR2 domain comprising the sequence set forth in SEQ ID NO:30, and a CDR3 domain comprising the sequence set forth in SEQ ID NO:31. The invention also features an antibody, or antigen-binding fragment thereof, which binds a plurality of β-chemokines, wherein said β-chemokines comprise MCP-1 and at least one other β-chemokine, and wherein said antibody or antigen-binding fragment comprises a light chain variable region having a CDR1 domain comprising the sequence set forth in SEQ ID NO:32, a CDR2 domain comprising the sequence set forth in SEQ ID NO:33, and a CDR3 &Instill comprising the sequence set forth in SEQ ID NO:34.

In still another embodiment, the invention features an antibody or antigen-binding fragment thereof, which binds a plurality of β-chemokines, wherein said β-chemokines comprise MCP-1 and at least one other β-chemokine, and wherein said antibody or antigen-binding fragment comprises a heavy chain variable region having a CDR1 domain comprising the sequence set forth in SEQ ID NO:29, a CDR2 domain comprising the sequence set forth in SEQ ID NO:30, and a CDR3 domain comprising the sequence set forth in SEQ ID NO:31, and a light chain variable region having a CDR1 domain comprising the sequence set forth in SEQ ID NO:32, a CDR2 domain comprising the sequence set forth in SEQ ID NO:33, and a CDR3 domain comprising the sequence set forth in SEQ ID NO:34. In one embodiment, at least one other β-chemokine is MCP-2.

In another embodiment, the antibody or antigen-binding fragment of the invention is modified to reduce or eliminate potential glycosylation sites. In still another embodiment, the constant region of the antibody, or fragment thereof of the invention is modified to reduce at least one constant region-mediated biological effector function relative to an unmodified antibody.

In yet another embodiment, the invention features a method of treating a subject suffering from a disorder selected from the group consisting of glomerulonephritis, scleroderma, cirrhosis, multiple sclerosis, lupus nephritis, atherosclerosis, inflammatory bowel disease or rheumatoid arthritis, comprising administering to the subject an antibody or fragment thereof of the invention.

The invention also provides a kit for detecting the presence of β-chemokines in a sample comprising reagents for performing an immunoassay; an antibody or antigen-binding fragment thereof that specifically binds to a plurality of β-chemokines comprising MCP-1 and at least one other β-chemokine; and reagents for detecting the binding of said antibody or antigen-binding fragment thereof.

BRIEF DESCRIPTION OF THE FIGURES

FIG. 3 graphically depicts the results of a chemotaxis assay of cells in response to MCP-1. FIG. 3A graphically depicts results using monoclonal antibodies 5D3-F7 (BD Biosciences, Pharmingen, San Diego, Calif.), 1M11, 3N10, 5J23, and 11K2 in response to 20 ng/mL of MCP-1. FIG. 3B graphically depicts results using 20 ng/mL of murine MCP-1 (JE) and monoclonal antibodies 2H5 (BD Biosciences, Pharmingen, San Diego, Calif.), 1M11, 3N10, 5123, and 11K2.

FIG. 6 graphically depicts results from a chemotaxis assay using pan-MCP antibodies demonstrating pan-MCP antibodies 11K2 and 1A1 increase MCP-2 mediated chemotaxis at low mAb concentrations (FIG. 6A). Blocking is also observed with MCP-2 mAb 281 (RD Systems, Minneapolis, Minn.). FIG. 6B graphically depicts a chemotaxis assay using the pan-MCP mAb 11K2 and the Fab fragment of 11K2.

FIG. 7 graphically depicts results from a MCP-2 calcium flux assay which depicts results from 55.5 nM of MCP-2 alone, depicts results which demonstrate that the 11K2 monoclonal antibody shows agonistic activity (FIG. 7B), and, as compared to 55.5 nM of MCP-2 alone (FIG. 7A), FIGS. 7C and 7D depict results which demonstrate that Fab and F(ab')2 fragments of 11K2 are inhibitory in this assay.

FIG. 8 shows the amino acid and nucleotide sequences of the variable heavy region of the murine 1A1 antibody (FIG. 8A), as well as the amino acid and nucleotide sequences of the 1A1 variable light region (FIG. 8B). CDR regions are underlined.

FIG. 9 shows the amino acid and nucleotide sequences of murine 11K2 variable heavy region (FIG. 9A), as well as the amino acid and nucleotide sequences of 11K2 variable light region (FIG. 9B). CDR regions are underlined.

DETAILED DESCRIPTION OF THE INVENTION

Figure 1:
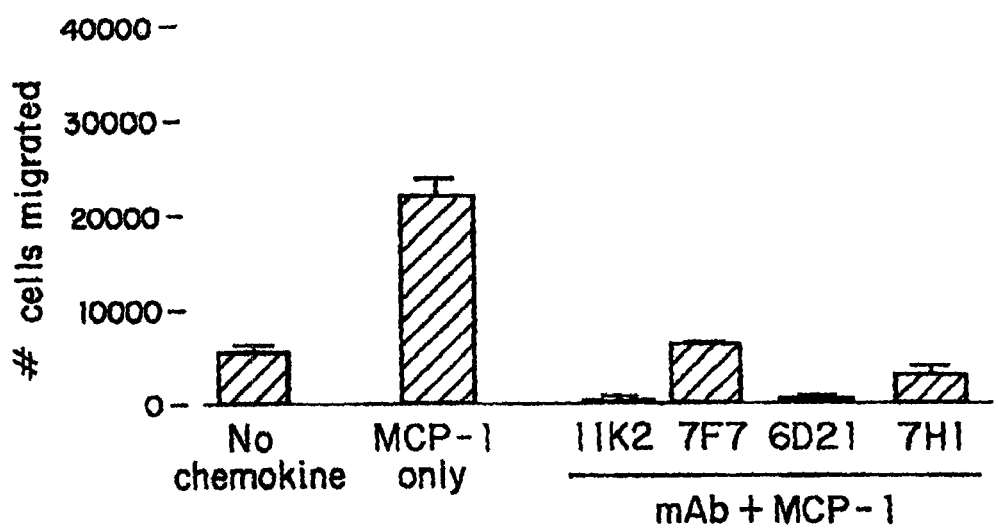
FIG. 1 graphically depicts the results of a chemotaxis assay using 11K2, 7F7, 6D21, and 7H1 hybridoma supernatant to inhibit chemotaxis in response to MCP-1. Each of the antibodies tested was able to inhibit MCP-1 induced chemotaxis, with 11K2 and 6D21 being the most effective.

The reference works, patents, patent applications, and scientific literature, including accession numbers to GenBank database sequences, that are referred to herein establish the knowledge of those with skill in the art are hereby incorporated by reference in their entirety to the same extent as if each was specifically and individually indicated to be incorporated by reference. Any conflict between any reference cited herein and the specific teachings of this specification shall be resolved in favor of the latter.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the alt. Any conflict between an art-understood definition of a word or phrase and a definition of the word or phrase as specifically taught in this specification shall be resolved in favor of the latter. Headings used herein are for convenience and are not to be construed as limiting.

Standard reference works setting forth the general principles of recombinant DNA technology known to those of skill in the art include Ausubel et al., CURRENT PROTOCOLS IN MOLECULAR BIOLOGY, John Wiley & Sons, New York, 1998; Sambrook et al., MOLECULAR CLONING: A LABORATORY MANUAL, 2d Ed., Cold Spring Harbor Laboratory Press, Plainview, N.Y., 1989; Kaufman et al, Eds., HANDBOOK OF MOLECULAR AND CELLULAR METHODS IN BIOLOGY AND MEDICINE, CRC Press, Boca Raton, 1995; McPherson, Ed., DIRECTED MUTAGENESIS: A PRACTICAL APPROACH, IRL Press, Oxford, 1991.

As used herein, the term "antibody" is meant to refer to complete, intact antibodies, and Fab, Fab', F(ab)$_2$, F$_v$, and other fragments thereof. Complete, intact antibodies include, for example, monoclonal antibodies such as murine monoclonal antibodies, chimeric antibodies, anti-idiotypic antibodies, anti-anti-idiotypic antibodies, and humanized antibodies.

As used herein, the term "binding" means the physical or chemical interaction between two proteins or compounds or associated proteins or compounds or combinations thereof. Binding includes ionic, non-ionic, hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated antibody-encoding nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

As used herein, the term "isolated antibody" refers to an immunoglobulin molecule or fragment thereof that has been removed from its native environment. This may include removing the antibody, or fragment thereof, from ascites fluid, serum, blood, or tissue culture fluid, for example.

As used herein, the term "β-chemokine" refers to a polypeptide containing four conserved cysteine residues characteristic of β-chemokines (e.g., as described in Van Coillie et al. (1999) Cytokine & Growth Factor Rev. 10:61-86), wherein the first two conserved cysteines are adjacent.

As used herein, the term "inhibiting the activity of β-chemokines" refers to causing a decrease in the relative activity of β-chemokines (e.g. MCP-1, MCP-2, mCP-3) in the presence of the antibody or antigen-binding fragment thereof in comparison with the activity observed in the absence of the antibody or antigen-binding fragment thereof.

As used herein, the term "sign of an inflammatory disorder" refers to observable or measurable indications of pathological inflammation, including, but not limited to edema, fever, emigration of leukocytes, proliferation of blood vessels, proliferation of connective tissue, redness, localized heat, exudation, and other signs as described in ROBBINS PATHOLOGIC BASIS OF DISEASE, 4$^{TH}$ EDITION, R. S. Cotran et al., Eds. W.B. Saunders, Co., 1989.

As used herein, the term "blocking chemotaxis" refers to a decrease in the relative amount of chemotactic activity of cells in the presence of the antibody or antigen-binding fragment thereof in comparison with chemotactic activity observed in the absence of the antibody or antigen-binding fragment thereof.

As used herein, the team "MCP MRHAS Motif" refers to an amino acid motif in human MCP-1 and MCP-3 termed Meningitis Related Homologous Antigenic Sequence. For human MCP-1, the MRHAS amino acid motif is Gln-Thr-Gln-Thr-Pro-Lys-Thr (SEQ ID NO:1); and for human MCP-3, the MRHAS motif is Lys-Thr-Gln-Thr-Pro-Lys-Leu (SEQ ID NO:2).

As used herein "conservative change" refers to alterations that are substantially conformationally or antigenically neutral; producing minimal changes in the tertiary structure of the mutant polypeptides, or producing minimal changes in the antigenic determinants of the mutant polypeptides, respectively, as compared to the native protein. Such conservative changes, when referring to chemokines refer to amino acid substitutions that do not ablate the activity of the subject chemokine, as measured by its ability to perform at least one function of the chemokine such as, but not limited to inducing chemotaxis, inducing enzyme or cytokine production, or binding to its receptor. When referring to the antibodies and antibody fragments of the invention, a conservative change means an amino acid substitution that does not render the antibody incapable of binding to the subject chemokine(s).

Those of ordinary skill in the art will be able to predict which amino acid substitutions can be made while maintaining a high probability of being conformationally and antigenically neutral. Such guidance is provided, for example in Berzofsky, (1985) Science 229:932-940 and Bowie et al. (1990) Science 247:1306-1310. Factors to be considered that affect the probability of maintaining conformational and antigenic neutrality include, but are not limited to (a) substitution of hydrophobic amino acids is less likely to affect antigenicity because hydrophobic residues are more likely to be located in a protein's interior, (b) substitution of physiochemically similar, amino acids is less likely to affect conformation because the substituted amino acid structurally mimics the native amino acid; and (c) alteration of evolutionarily conserved sequences is likely adversely affect conformation as such conservation suggests that the amino acid sequences may have functional importance.

One of ordinary skill in the art will be able to assess alterations in protein conformation using well-known assays, such as, but not limited to microcomplement fixation methods (Wasserman et al. (1961) J. Immunol. 87:290-295; Levine et al. (1967) Meth. Enzymol. 11:928-936) and through binding studies using conformation-dependent monoclonal antibodies (Lewis et al. (1983) Biochem. 22:948-954).

As used herein, "therapeutic composition" refers to a composition which directly or indirectly ameliorates a disease condition. That is, administration of the composition alleviates at least one symptom of a disease or disorder.

As used herein, "immunoaffinity resin" refers to a solid substrate to which at least one antibody is bound via a region other than its antigen combining site, thereby allowing the bound antibody to bind to its epitope. Many resins are known in the art and are routinely used to form immunoaffinity resins. Any such resin may be used to form the immunoaffinity resins of the invention.

Antibodies and Antibody Fragments

The invention provides antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies), including compounds which include CDR sequences which specifically recognize a plurality of β-chemokines, particularly monocyte chemotactic proteins (e.g., MCP-1, MCP-2, and MCP-3) or fragments thereof.

Antibody fragments, including Fab, Fab', F(ab')$_2$, and F$_v$, are also provided by the invention. The term "specific for," when used to describe antibodies of the invention, indicates that the antibody exhibits appreciable affinity for antigen or a preferred epitope, i.e. plurality of β-chemokines, and, preferably, does not exhibit crossreactivity (i.e., are able to distinguish β-chemokines from other polypeptides by virtue of measurable differences in binding affinity, despite the possible existence of localized sequence identity, homology, or similarity between tβ-chemokines and such polypeptides).

It will be understood that specific antibodies may also interact with other proteins (for example, *Staphylococcus aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6. Antibodies that recognize and bind fragments of the β-chemokines are also contemplated, provided that the antibodies are specific for β-chemokines. Antibodies of the invention can be produced using any method well known and routinely practiced in the art.

For the production of polyclonal antibodies, various suitable host animals (e.g., rabbit, goat, mouse or other mammal) may be immunized by injection with the native protein, or a synthetic variant thereof, or a derivative of a β-chemokine or combination of more than one β-chemokine. For example, but not by way of limitation, a cocktail of MCP-1, MCP-2 and MCP-3 may be used as an immunogen to induce an immune response against these β-chemokines.

An appropriate immunogenic preparation can contain, for example, a preparation of isolated, native β-chemokines, recombinantly expressed monocyte chemotactic proteins or chemically synthesized β-chemokines. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, plutonic polyols, polyanions, peptides, oil emulsions, dinitrophenol etc.), human adjuvants such as Bacille Calmette-Guerin and *Corynebacterium parvum*, or similar immunostimulatory agents. If desired, the antibody molecules directed against the β-chemokines can be isolated from the mammal (e.g., from the blood) and further purified by well-known techniques, such as protein A chromatography to obtain the immunoglobulin fraction.

The term "monoclonal antibody" or "monoclonal antibody composition," as used herein, refers to a population of antibody molecules that contain only one species of an antigen-binding site capable of immunoreacting with a particular epitope of a β-chemokine. A monoclonal antibody composition thus typically displays a single binding affinity for a particular epitope of a β-chemokine with which it immunoreacts. The pan-antibodies of the invention specifically recognize and specifically bind to more than one type of β-chemokine. For preparation of monoclonal antibodies directed towards a particular β-chemokine, or derivatives, fragments, analogs or homologs thereof, any technique that provides for the production of antibody molecules by continuous cell line culture may be utilized. Such techniques include, but are not limited to, the hybridoma technique (see Kohler & Milstein (1975) *Nature* 256:495-497); the trioma technique; the human B-cell hybridoma technique (see Kozbor, et al. (1983) *Immunol. Today* 4:72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96) Human monoclonal antibodies may be utilized in the practice of the present invention and may be produced by using human hybridomas (see Cote, et al., 1983. *Proc. Natl. Acad. Sci. USA* 80: 2026-2030) or by transforming human B-cells with Epstein Barr Virus in vitro (see Cole, et al. (1985) In: MONOCLONAL ANTIBODIES AND CANCER THERAPY, Alan it Liss, Inc., pp. 77-96).

In certain embodiments the antibodies, and fragments thereof, bind to regions in the β-chemokines (e.g., MCP-1, MCP-2 and MCP-3). In some embodiments, the antibodies or antigen-binding fragments thereof bind MCP-2 and at least one other β-chemokine (e.g., MCP-1 or MCP-3). Thus, in some embodiments, the antibodies or fragments thereof bind MCP-1 and MCP-2 and in other embodiments the antibodies or fragments thereof bind MCP2 and MCP-3. In other embodiments, the antibodies or antigen-binding fragments thereof bind MCP-1, MCP-2 and MCP-3. In other embodiments, the antibodies or antigen-binding fragments thereof bind MCP-1 and MCP-3 other than to regions containing the MRHAS motifs, QTQTPKT (MCP-1) and KTQTPKL (MCP-3).

In certain embodiments, the antibodies or antigen-binding fragments thereof comprise antibodies selected from the group consisting of 11K2.1 (ATCC Accession No. PTA-3987), 61321.1 (ATCC Accession No. PTA-3989), 4N4.1 (ATCC Accession No. PTA-3994), 5A13.1 (ATCC Accession No. PTA-3995), 7H1.1 (ATCC Accession No. PTA-3985), 1A1.1 (ATCC Accession No. PTA-3990), 6I5.1 (ATCC Accession No. PTA-3986), 2O24.1 (ATCC Accession No. PTA-3993), 9B11.1 (ATCC Accession No. PTA-3992), 9B12.1 (ATCC Accession No. PTA-3996), 9C11.1 (ATCC Accession No. PTA-3988), and 12F15.1 (ATCC Accession No. PTA-3991), or antigen-binding fragments of these antibodies.

The amino acid and nucleotide sequences of the light and heavy variable regions of antibody 1A1 are shown in FIG. 8, where the CDRs are underlined. The amino acid sequence of the 1A1 heavy chain variable region is set forth as SEQ ID NO:11 and the light chain variable region of 1A1 is set forth as SEQ ID NO:12. Furthermore, the CDRs of antibody 1A1 are described as SEQ ID NOs: 13-15 (heavy chain variable region) and SEQ ID NOs:16-18 (light chain variable region).

In one embodiment, the invention features an antibody, or antigen-binding fragment comprising the variable heavy chain region described in SEQ ID NO:11 and the variable light chain region described in SEQ ID NO:12. In another embodiment, the invention features an antibody or antigen-binding fragment comprising CDRs from the 1A1 heavy chain variable region as described in SEQ ID NO:11, and CDRs from the 1A1 light chain variable region as described in SEQ ID NO:12.

The amino acid and nucleotide sequences of the light and heavy variable regions of antibody 11K2 are shown in FIG. 9, where the CDRs are underlined. The amino acid sequence of the 11K2 heavy chain variable region is set forth as SEQ ID NO:27 and the light chain variable region of 11K2 is set forth as SEQ ID NO:28. In addition, the CDRs of antibody 11K2 are described as SEQ ID NOs:29-31 (heavy chain variable region) and SEQ ID NOs:32-34 (light chain variable region).

In one embodiment, the invention features an antibody, or antigen-binding fragment comprising the variable heavy chain region described in SEQ ID NO:27 and the variable light chain region described in SEQ ID NO:28. In another embodiment, the invention features an antibody or antigen-binding fragment comprising CDRs from the 11K2 heavy chain variable region as described in SEQ ID NO:27, and CDRs from the 1A1 light chain variable region as described in SEQ ID NO:28.

In producing the antibodies of the invention, the immunogens may be a preparation containing at least one β-chemokine, preferably more than one β-chemokine. In some embodiments, the β-chemokines are human monocyte chemotactic proteins (MCPs), including MCP-1, MCP-2 and MCP-3. The β-chemokines may be native or recombinantly produced β-chemokines. In some embodiments, the immunogens may be antigenic fragments of tβ-chemokines, such as fragments of MCPs which may optionally be conjugated to a carrier molecule to impart a stronger immune response upon administration to an animal. The β-chemokine immunogens, such as MCPs may contain additions, deletions and/or substitutions of amino acids, provided that the alterations do not ablate antigenicity of the mutated β-chemokines such that antibodies against the mutant versions do not bind native β-chemokines. Preferably, the amino acid substitutions are conservative changes in the amino acid sequence, provided the MCP molecules remain antigenic.

The sequences of MCP proteins and polynucleotides encoding such proteins are known and may be found, for example, in publicly available sequence databases such as GenBank. In addition, the sequences of various MCPs have been published, and may be found, for example, in Furutani et al. (1989) *Biochem. Biophys. Res. Commun.* 159:249-255, Yoshimura et al. (1989) *FEBS Lett.* 244:487-493 (MCP-1); Van Collie et al. (1997) *Biochem. Biophys. Res. Commun.* 231:726-730, Van Collie et al. (1997) *Genomics* 21:323-331 (MCP-2); Opdenakker et al. (1993) *Biochem Biophys. Res. Commun.* 191:535-542, Opdenakker et al. (1993) *Genomics* 21:403-408 (MCP-3), the disclosure of each of which is incorporated by reference herein in its entirety.

The antibodies of the invention may be any isotype, including IgA, IgD, IgE, IgG1, IgG2, IgG2a, IgG2b, IgG3, or IgM. The isotypes may be changed by isotype switching techniques as is known in the art or may be genetically engineered by CDR grafting, chimeric antibody formation or humanization.

According to the invention, techniques can be adapted for the production of single-chain antibodies specific to β-chemokines (see e.g., U.S. Pat. No. 4,946,778). In addition, methods can be adapted for the construction of Fab expression libraries (see e.g., Huse, et al. (1989) *Science* 246:1275-1281) to allow rapid and effective identification of monoclonal Fab fragments with the desired specificity for β-chemokines or derivatives, fragments, analogs or homologs thereof. Non-human antibodies can be "humanized" by techniques well known in the art (see e.g., U.S. Pat. No. 5,225,539). In one method, the non human CDRs are inserted into a human antibody or consensus antibody framework sequence. Further changes can then be introduced into the antibody framework to modulate affinity or immunogenicity. Antibody fragments that contain the idiotypes to β-chemokines may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) $F_v$ fragments.

Additionally, recombinant anti-β-chemokine antibodies, such as chimeric and humanized monoclonal antibodies, comprising both human and non-human portions, which can be made using standard recombinant DNA techniques, are within the scope of the invention. Chimeric and/or humanized antibodies have the same or similar binding specificity and affinity as a mouse or other nonhuman antibody that provides the starting material for construction of a chimeric or humanized antibody.

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immunogenicity.

Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood a al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al., (1988) *Science* 239:1534; and Beidler et al. (1988) *J. Immunol.* 141:4053-4060, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539.

The CDRs of the 1A1 antibody can be used to produce humanized and chimeric antibodies. In one embodiment, the invention provides an isolated antibody, or antigen-binding fragment thereof, which binds a plurality of β-chemokines, wherein said β-chemokines comprise MCP-1 and at least one other β-chemokine (e.g. MCP-2, MCP-3), and wherein the antibody or antigen-binding fragment comprises at least one of the following CDRs: CDR1, CDR2, or CDR3, from the 1A1 heavy chain variable region set forth as SEQ ID NO:11. In another embodiment, the invention provides an isolated antibody, or antigen-binding fragment thereof, which binds a plurality of β-chemokines, wherein said β-chemokines comprise MCP-1 and at least one other β-chemokine (e.g. MCP-2, MCP-3), which comprises at least one of the following CDR combinations: CDR1 and CDR2; CDR1 and CDR3; CDR2 and CDR3; or CDR1, CDR2, and CDR3, from the 1A1 heavy chain variable region described in SEQ ID NO:11.

In one embodiment, the antibody of the invention is a chimeric antibody. In another embodiment, the antibody of the invention is a humanized antibody.

The invention also provides an isolated antibody, or antigen-binding fragment thereof, which binds a plurality of β-chemokines, wherein said β-chemokines comprise MCP-1 and at least one other β-chemokine (e.g. MCP-2, MCP-3), wherein the antibody or antigen-binding fragment comprises at least one of the following CDRs: CDR1, CDR2, or CDR3, from the 1A1 light chain variable region described in SEQ ID NO:12. In another embodiment, the invention provides an isolated antibody, or antigen-binding fragment thereof, which binds a plurality of β-chemokines, wherein said β-chemokines comprise MCP-1 and at least one other β-chemokine (e.g. MCP-2, MCP-3), wherein the antibody or antigen-binding fragment comprises at least one of the following CDR combinations: CDR1 and CDR2; CDR1 and CDR3; CDR2 and CDR3; or CDR1, CDR2, and CDR3, from the 1A1 light chain variable region described in SEQ ID NO:12. In one embodiment, the antibody of the invention is a chimeric antibody. In another embodiment, the antibody of the invention is a humanized antibody.

In one embodiment, the invention provides an antibody or antigen-binding fragment which binds a plurality of β-chemokines, wherein said β-chemokines comprise MCP-1 and at least one other β-chemokine (e.g., MCP-2, MCP-3), and wherein said antibody or antigen-binding fragment comprises a heavy chain variable region having a CDR1 domain comprising the sequence set forth as SEQ ID NO:13, a CDR2 domain comprising the sequence set forth as SEQ ID NO:14, and a CDR3 domain comprising the sequence set forth as SEQ ID NO:15. In another embodiment, the invention features an antibody or antigen-binding fragment which binds a plurality of β-chemokines, wherein said β-chemokines comprise MCP-1 and at least one other β-chemokine (e.g., MCP-2, MCP-3), and wherein said antibody or antigen-binding fragment comprises a light chain variable region having a CDR1 domain comprising the sequence set forth as SEQ ID NO:16, a CDR2 domain comprising the sequence set forth as SEQ ID NO:17, and a CDR3 domain comprising the sequence set forth as SEQ ID NO:18. In another embodiment, the CDR domains of the 1A1 antibody, set forth as SEQ ID NOs:13-18, are used to make a chimeric antibody. In yet another embodiment, the CDR domains of the 1A1 antibody, set forth as SEQ ID NOs:13-18, are used to make a humanized antibody.

The CDRs of the 11K2 antibody can be also used to produce humanized and chimeric antibodies. The invention features an isolated antibody or antigen-binding fragment thereof which binds a plurality of (β-chemokines, wherein said β-chemokines comprise MCP-1 and at least one other β-chemokine (e.g., MCP-2, MCP-3), and wherein said antibody or antigen-binding fragment comprises at least one of the following CDRs: CDR1, CDR2, or CDR3, from the 11K2 heavy chain variable region set forth as SEQ ID NO:27. In an additional embodiment, the invention features an isolated antibody or antigen-binding fragment thereof which binds a plurality of β-chemokines, wherein said β-chemokines comprise MCP-1 and at least one other β-chemokine (e.g., MCP-2, MCP-3), and wherein said antibody or antigen-binding fragment comprises at least one of the following CDR combinations: CDR1 and CDR2; CDR1 and CDR3; CDR2 and CDR3; or CDR1, CDR2, and CDR3, from the 11K2 heavy chain variable region described in SEQ ID NO:27. In one embodiment, the antibody of the invention is a chimeric antibody. In another embodiment, the antibody of the invention is a humanized antibody.

The invention also provides an isolated antibody, or antigen-binding fragment thereof which binds a plurality of β-chemokines, wherein said chemokines comprise MCP-1 and at least one other β-chemokine (e.g. MCP-2, MCP-3), and wherein said antibody or antigen-binding fragment comprises at least one of the following CDRs: CDR1, CDR2, or CDR3, from the 11K2 light chain variable region set forth as SEQ ID NO:28. In another embodiment, the invention provides an isolated antibody, or antigen-binding fragment thereof which binds a plurality of β-chemokines, wherein said β-chemokines comprise MCP-1 and at least one other β-chemokine (e.g. MCP-2, MCP-3), and wherein said antibody or antigen-binding fragment comprises at least one of the following CDR combinations: CDR1 and CDR2; CDR1 and CDR3; CDR2 and CDR3; or CDR1, CDR2, and CDR3, from the 11K2 light chain variable region described in SEQ ID NO:28. In one embodiment, the antibody of the invention is a chimeric antibody. In another embodiment, the antibody of the invention is a humanized antibody.

In another embodiment, the invention features an antibody or antigen-binding fragment thereof which binds a plurality of β-chemokines, wherein said β-chemokines comprise MCP-1 and at least one other β-chemokine (e.g., MCP-2, MCP-3), and wherein said antibody or antigen-binding fragment comprises a heavy chain variable region having a CDR1 domain comprising the sequence set forth as SEQ ID NO:29, a CDR2 domain comprising the sequence set forth as SEQ ID NO:30, and a CDR3 domain comprising the sequence set forth as SEQ ID NO:31. In another embodiment, the invention features an antibody or antigen-binding fragment thereof which binds a plurality of β-chemokines, wherein said β-chemokines comprise MCP-1 and at least one other β-chemokine (e.g., MCP-2, MCP-3), and wherein said antibody or antigen-binding fragment comprises a light chain variable region having a CDR1 domain comprising the sequence set forth as SEQ ID NO:32, a CDR2 domain comprising the sequence set forth as SEQ ID NO:33, and a CDR3 domain comprising the sequence set forth as SEQ ID NO:34: In another embodiment, the CDR domains of the 11K2 antibody, as described in SEQ ID NOs:29-34, are used to make a chimeric antibody. In yet another embodiment, the CDR domains of the 11K2 antibody, as described in SEQ ID NOs: 29-34, are used to make a humanized antibody.

In general, humanized antibodies are produced by substituting mouse CDRs into a human variable domain framework which is most likely to result in retention of the correct spatial orientation of the CDRs if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4:773 (1991); Kolbinger et al., *Protein Engineering* 6:971 (1993) and Carter et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid:

noncovalently binds antigen directly,
is adjacent to a CDR region,
otherwise interacts with a CDR region (e.g., is within about 3-6 Å of a CDR region as determined by computer modeling), or
participates in the VL-VH interface.

Residues which "noncovalently bind antigen directly" include amino acids in positions in framework regions which are have a good probability of directly interacting with amino acids on the antigen according to established chemical forces, for example, by hydrogen bonding, Van der Wags forces, hydrophobic interactions, and the hie.

Residues which are "adjacent to a CDR region" include amino acid residues in positions immediately adjacent to one or more of the CDRs in the primary sequence of the humanized immunoglobulin chain, for example, in positions immediately adjacent to a CDR as defined by Rabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to effect a CDR region. In one embodiment, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (Å) of some atom in the CDRs and must contain an atom that could interact with the CDR atoms according to established chemical forces, such as those listed above.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

Residues which "participate in the VL-VH intetface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, gin; asn, gln; ser, thr; lys, arg; and phe, tyr.

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criterion help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions.

Additional candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence which enhance activity. Unusual residues that are predicted to affect binding are retained, whereas residues predicted to be unimportant for binding can be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

In a preferred embodiment, humanized antibodies preferably exhibit a specific binding affinity for antigen similar to that of the mouse antibody from which they were constructed. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabelled reagents) or competitive binding assays.

In some embodiments, the chimeric proteins of the invention comprise an antigen-binding fragment of an antibody joined via peptide bonds to a heterologous protein. In such embodiments, the antigen-binding portion of the antibody binds MCP-2 and at least one other β-chemokine, such as MCP-1 or MCP-3. In some embodiments, the antigen-binding fragment of the antibody binds MCP-1, MCP-2 and MCP-3. In other embodiments, the antigen-binding fragment binds MCP-1 and MCP-3, but does not bind an MCP MRHAS motif.

In some embodiments, the heterologous proteins that are joined to the antigen-binding fragments of the antibodies of the invention are enzymes, toxins or a cytokine.

The invention also provides compositions comprising a chimeric protein of the invention and at least one pharmaceutically acceptable carrier, as defined herein.

The invention also provides for antibodies, antigen-binding fragments and/or antibody fragments of the invention that have high binding affinity for β-chemokines. High binding affinity refers to binding affinities of, for example, about $10 \times 10^{-12}$ M (i.e. 10 pM) or less. In one embodiment the antibodies, antigen-binding fragments and/or antibody fragments have a Kd for binding to the β-chemokines (either binding a plurality of MCP's selected from MCP-1, MCP-2, and MCP-3 or that bind the individual MCPs, i.e. an antibody or antigen-binding fragment that binds to MCP-1, MCP-2 or MCP-3) between about $10 \times 10^{-12}$ M (10 pM) and about $8 \times 10^{-12}$ M (8 pM) including $9 \times 10^{-1}$ M (9 pM); alternatively between about $9 \times 10^{-12}$ M (9 pM) and about $7 \times 10^{-12}$ M (7 pM) including $8 \times 10^{-12}$ M (8 pM); alternatively between about $8\times10^{-12}$ M (8 pM) and about $6\times10^{-12}$ M (6 pM) including $7\times10^{-12}$ M (7 pM); alternatively between about $7\times10^{-12}$M (7 pM) and about $5\times10^{-12}$ M (5 pM) including $6\times10^{-12}$ M (6 pM), alternatively between about $6\times10^{-12}$ M (6 pM) and about $4\times10^{-12}$M (4 pM) including $5\times10^{-12}$ M (5 pM), alternatively between about $5\times10^{-12}$ M (5 pM) and about $3\times10^{-12}$ M (3 pM) including $4\times10^{-12}$M (4 pM); alternatively between about $4\times10^{-12}$ M (4 pM) and about $2\times10^{-12}$ M (2 pM) including $3\times10^{-12}$M (3 pM); alternatively between about $3\times10^{-12}$ M pM) and about $3\times10^{-12}$ M (1 pM) including $2\times10^{-12}$ M (2 pM); alternatively about $1\times10^{-12}$ M (1 pM) and about $8\times10^{13}$M (0.8 pM) including $9\times10^{-13}$ M (0.9 pM); alternatively between about $9\times10^{-13}$ M (0.9 pM) and about $7\times10^{-13}$ M (0.7 pM) including $8\times10^{-13}$ M (0.8 pM); alternatively between about $8\times10^{-13}$ M (0.8 pM) and about $6\times10^{-13}$ M (0.6 pM) including $7\times10^{-13}$ M (0.7 pM); alternatively between about $7\times10^{-13}$ M (0.7 pM) and about $5\times10^{-13}$ M (0.5 pM) including $6\times10^{-13}$ M (0.6 pM), alternatively between about $6\times10^{-13}$ M (0.6 pM) and about $4\times10^{-13}$ M (0.4 pM) including $5\times10^{-13}$ M (0.5 pM), alternatively between about $5\times10^{-13}$M (0.5 pM) and about $3\times10^{-13}$ M (0.3 pM) including $4\times10^{-13}$ M (0.4 pM); alternatively between about $4\times10^{-13}$M (A pM) and about $2\times10^{-13}$ M (2 pM) including $3\times10^{-13}$ M (0.3 pM); alternatively between about $3\times10^{-13}$ M (0.3 pM) and about $1\times10^{-13}$ M (0.1 pM) including $2\times10^{-13}$ M (0.2 pM). The invention would include for example an antibody or antigen-binding fragment thereof that binds to MCP-1, MCP-2 or MCP-3 wherein the antibody or antigen-binding fragment thereof has a Kd for binding to MCP-1, MCP-2 or MCP-3 selected from the following Kd's: about $10\times10^{-13}$ M (1 pM), 9×10–13 M (0.9 pM), $8\times10^{-13}$ M (0.8 pM), $7\times10^{-13}$ M (0.7 pM), $6\times10^{-13}$M (0.6 pM), $5\times10^{-13}$ M (0.5 pM), $4\times10^{-13}$ M (0.4 pM), $3\times10^{-13}$ M (0.3 pM), $2\times10^{-13}$ M (0.2 pM) or $1\times10^{-13}$ M (0.1 pM). (An example of such an antibody would include for example 11K2 in which the antibody has a binding affinity for human MCP-1 of about 0.4 pM.) The invention would also include for example an antibody or antigen-binding fragment thereof that binds to a plurality of MCP's (i.e. MCP-1 and MCP-2 or MCP-1 and MCP-3 or MCP-1, MCP-2 and MCP-3 or MCP-2 and MCP-3) wherein the antibody or antigen-binding fragment thereof has a Kd for binding to at least one of the MCP's (i.e. MCP-1, MCP-2 or MCP-3) selected from the following Kd's: about $10\times10^{13}$M (1 pM), $9\times10^{-13}$ M (0.9 pM), 8×M (0.8 pM), $7\times10^{-13}$ M (0.7 pM), $6\times10^{-13}$ M (0.6 pM), $5\times10^{-13}$ M (0.5 pM), $4\times10^{-13}$M (0.4 pM), $3\times10^{-13}$M (0.3 pM), $2\times10^{-13}$ M (0.2 pM) or $1\times10^{-13}$ M (0.1 pM). (An example of such an antibody would also include for example 11K2 in which the antibody has a binding affinity for human MCP-1 of about 0.4 pM. and also binds MCP-2 and MCP-3). Methods for measuring the binding affinity of the antibody, antigen-binding fragment and or antibody fragment for the various β-chemokine(s) are known to those of skill in the art and include, for example, the kinetic exclusion assay illustrated in Example 4 herewith.

The invention also provides for antibodies, antigen-binding fragments and/or antibody fragments comprising a Fab fragment wherein the Fab fragment has a Kd for binding MCP-1, MCP-2 or MCP-3 of, for example, about $1.5\times10^{-11}$ M (i.e. 15 pM) or less.

The invention would include for example an antibody, antigen-binding fragment and/or antibody fragment thereof wherein the Fab fragment has a Kd for binding to MCP-1, MCP-2 or MCP-3 selected from the following Kd's: about $1.8\times10^{-11}$ M (18 pM), about $1.7\times10^{-11}$ M (17 pM), about $1.6\times10^{-11}$ M (15 pM), about $1.5\times10^{-11}$M (15 pM), $1.4\times10^{-11}$M (14 pM), $13\times10^{-11}$M (13 pM), $1.2\times10^{-11}$ M (12 pM), $1.1\times10^{-11}$M (11 pM), $1\times10^{-11}$ M (10 pM), $0.9\times10^{-11}$M (9 pM), $0.8\times10^{-11}$M (8 pM), $0.7\times10^{-11}$M (7 pM), $0.6\times10^{-11}$M (6 pM), $0.5\times10^{-11}$M (5 pM), $0.4\times10^{-11}$M (4 pM), $0.3\times10^{-11}$M (3 pM), $0.2\times10^{-11}$M (2 pM) or $0.1\times10^{-11}$ M (1 pM). Methods for measuring the binding affinity of the antibody, antigen-binding fragment and or antibody fragment are known to those of skill in the art and include, for example, the kinetic exclusion assay illustrated in Example 4 herewith.

The invention also provides for antibodies, antigen-binding fragments and/or antibody fragments that have the following binding affinity for the β-chemokines (either binding a plurality of MCP's selected from MCP-1, MCP-2, and MCP-3 or that bind the individual MCPs, i.e. an antibody or antigen-binding fragment that binds to MCP-1, MCP-2 or MCP-3). In one embodiment the binding affinity is between about $5\times10^{-8}$ M and about $5\times10^{-12}$ M, in some embodiments the binding affinity is about $5\times10^{-9}$ M to about $5\times10^{-11}$M, in some embodiments the binding affinity is about $5\times10^{-7}$ M to about $5\times10^{-8}$ M, in some embodiments the binding affinity is about $5\times10^{-8}$ M to about $5\times10^{-9}$ M, in some embodiments the binding affinity is about $5\times10^{-9}$ M to about $5\times10^{-10}$ M, in some embodiments the binding affinity is about $5\times10^{-10}$ M to about $5\times10^{-11}$ M.

The antibodies and antibody fragments of the invention can out-compete for the binding of ligand than other, known anti-β-chemokine antibodies with an $IC_{50}$ of less than about 10 μg/ml, more preferably less than about 5 μg/ml, more preferably less than about 4 μg/ml, more preferably less than about 3 μg/ml, more preferably less than about 2 μg/ml, and more preferably less than about 1.0 μg/ml.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of β-chemokines is facilitated by generation of hybridomas that bind to the fragment of β-chemokines possessing such a domain. Antibodies that are specific for one or more domains within β-chemokines, e.g., conserved domains of β-chemokine family proteins, or derivatives, fragments, analogs or homologs thereof, are also provided herein.

Anti-β-chemokine pan-antibodies may be used in methods known within the art relating to the localization and/or quantitation of a Jβ-chemokines (e.g., for use in measuring levels of β-chemokines within appropriate physiological samples, for use in diagnostic methods, for use in imaging the protein, and the like). In a given embodiment, antibodies for β-chemokines, or derivatives, fragments, analogs or homologs thereof, that contain the antibody derived binding domain, are utilized as pharmacologically-active compounds (hereinafter "Therapeutics").

An anti-β-chemokine pan-antibody (e.g., monoclonal antibody) can be used to isolate β-chemokines by standard techniques, such as affinity chromatography or immunoprecipitation. An anti-β-chemokine pan-antibody can facilitate the purification of natural β-chemokines from cells and of recombinantly produced β-chemokines expressed in host cells. Moreover, an anti-β-Chemokine pan-antibody can be used to detect β-chemokines (e.g., in a cellular lysate or cell supernatant) in order to evaluate the abundance and pattern of expression of the β-chemokines. Anti-β-chemokine pan-antibodies can be used diagnostically to monitor protein levels in tissue as part of a clinical testing procedure in order to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorottiazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

In addition, the antibodies of the present invention may be conjugated to toxins such as radioisotopes, protein toxins and chemical toxins which may be conjugated to antibodies. Such toxins include, but are not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, Boron-10, Actinide, ricin, adriamycin, calicheamicin, and 5-fluorouracil.

Another aspect of the present invention is directed to methods of inducing an immune response in a mammal against a polypeptide of the invention by administering to the mammal an amount of the polypeptide preparation sufficient to induce an immune response. The amount will be dependent on the animal species, size of the animal, and the like but can be determined by those skilled in the art.

Anti-Idiotypic Antibodies

Another aspect of the invention is directed to anti-idiotypic antibodies and anti-anti-idiotypic antibodies. An anti-idiotypic antibody is an antibody that recognizes determinants of another antibody (a target antibody). Generally, the anti-idiotypic antibody recognizes determinants of the antigen-binding site of the target antibody. Typically, the target antibody is a monoclonal antibody. An anti-idiotypic antibody is generally prepared by immunizing an animal (particularly, mice) of the same species and genetic type as the source of the target monoclonal antibody, with the target monoclonal antibody. The immunized animal mounts an immune response to the idiotypic determinants of the target monoclonal antibody and produces antibodies against the idiotypic determinants of the target monoclonal antibody. Antibody-producing cells, such as splenic cells, of the immunized animal may be used to generate anti-idiotypic monoclonal antibodies. Furthermore, an anti-idiotypic antibody may also be used to immunize animals to produce anti-anti-idiotypic antibodies. These immunized animals may be used to generate anti-anti-idiotypic monoclonal antibodies using standard techniques. The anti-anti-idiotypic antibodies may bind to the sauce epitope as the original, target monoclonal antibody used to prepare the anti-idiotypic antibody. The anti-anti-idiotypic antibodies represent other monoclonal antibodies with the same antigen specificity as the original target monoclonal antibody.

If the binding of the anti-idiotypic antibody with the target antibody is inhibited by the relevant antigen of the target antibody, and if the anti-idiotypic antibody induces an antibody response with the same specificity as the target antibody, it mimics the antigen of the target antibody. Such an anti-idiotypic antibody is an "internal image anti-idiotype" and is capable of inducing an antibody response as if it were the original antigen. (Bona and Kohler, ANTI-IDIOTYPIC ANTIBODIES AND INTERNAL IMAGE, IN MONOCLONAL AND ANTI-IDIOTYPIC ANTIBODIES: PROBES FOR RECEPTOR STRUCTURE AND FUNCTION, Venter J. C., Frasser, C. M., Lindstrom, J. (Eds.), Alan R. Liss, N.Y., 1984. pp 141-149). Vaccines incorporating internal image anti-idiotype antibodies have been shown to induce protective responses against viruses, bacteria, and parasites (Kennedy et al. (1986) 232:220-223; McNamara et al. (1985) *Science* 226:1325-1326). Internal image anti-idiotypic antibodies have also been shown to induce immunity to tumor related antigens (Raychauhuri et al. (1986) *J. Immunol.* 137:1743-1749; Raychauhuri et al. (1987) *J. Immunol.* 139:3902-3910; Bhattacharya-Chatterjee et al. (1987) *J. Immunol.* 139:1354-1360; Bhattacharya-Chatterjee et al. (1988) *J. Immunol.* 141: 1398-1403; Herlyn, D. et al. (1989) *Intern. Rev. Immunol.* 4:347-357; Chen, Z-J et al. (1990) *Cell Imm. Immunother. Cancer* 351-359; Herlyn, D. et al. (1991) In Vivo 5:615-624; Furuya et al., (1992) *Anticancer Res.* 12:27-32; Mittelman, A. et al., (1992) *Proc. Natl. Acad. Sci., USA* 89:466-470; Durrant, L. G. et al. (1994) *Cancer Res.* 54:4837-4840; Mittelman, A. et al. (1994) *Cancer Res.* 54:415-421; Schmitt, H. et al. (1994) *Hybridoma* 13:389-396; Chakroborty, M. et al. (1995) *J. Immunother.* 18:95-103; Chakrobarty, M. et al., (1995) *Cancer Res.* 55:1525-1530; Foon, K. A. et al. (1995) *Clin. Cancer Res.* 1:1205-1294; Herlyn, D, et at. (1995) *Hybridoma* 14:159-166; Sclebusch, H. et al. (1995) *Hybridoma* 14:167-174; Herlyn, D. et al. (1996) *Cancer Immunol Immunother.* 43:65-76).

Anti-idiotypic antibodies for β-chemokines may be prepared, for example, by immunizing an animal, such as a mouse, with a immunogenic amount of a composition comprising β-chemokines or immunogenic portions thereof, containing at least one antigenic epitope of β-chemokines. The composition may also contain a suitable adjuvant, and any carrier necessary to provide immunogenicity. Monoclonal antibodies recognizing β-chemokines may be prepared from the cells of the immunized animal as described above. A monoclonal antibody recognizing a common epitope of β-chemokines is then selected and used to prepare a composition comprising an immunogenic amount of the anti-β-chemokine monoclonal antibody. Typically, a 25 to 200 μg dose of purified β-chemokine monoclonal would be sufficient in a suitable adjuvant.

Animals may be immunized 2-6 times at 14 to 30 day intervals between doses. Typically, animals are immunized by any suitable route of administration, such as intraperitoneal, subcutaneous, intravenous or a combination of these. Anti-idiotypic antibody production may be monitored during the immunization period using standard immunoassay methods. Animals with suitable titers of antibodies reactive with the target monoclonal antibodies may be re-immunized with the monoclonal antibody used as the immunogen three days before harvesting the antibody producing cells. Preferably, spleen cells are used, although other antibody producing cells may be selected. Antibody-producing cells are harvested and fused with myeloma cells to produce hybridomas, as described above, and suitable anti-idiotypic antibody-producing cells are selected.

Anti-anti-idiotypic antibodies are produced by another round of immunization and hybridoma production by using the anti-idiotypic monoclonal antibody as the immunogen.

Expression of Recombinant Antibodies

Chimeric, humanized, and human antibodies as well as antigen-binding fragments thereof, are typically produced by recombinant expression. Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

Chemical Modifications

In some embodiments, the antibodies and antibody fragments of the invention may be chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat conditions that may be alleviated or modulated by administration of the antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In other embodiments of the invention the antibodies or antigen-binding fragments thereof are conjugated to albumen using art recognized techniques.

In another embodiment of the invention, antibodies, or fragments thereof, are modified to reduce or eliminate potential glycosylation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis (see http://www.cbs.dtu.dk/services/NetNGlyc/ for predicting N-linked glycoslyation sites) and http://www.cbs.dtu.dk/services/NetOGlyc/ for predicting O-linked glycoslyation sites). Additional methods for altering glycosylation sites of antibodies are described in U.S. Pat. Nos. 6,350,861 and 5,714,350.

In yet another embodiment of the invention, antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

Therapeutics

Antibodies or antigen-binding fragments of the invention are useful for, e.g., therapeutic purposes (by modulating activity of monocyte chemotactic proteins), diagnostic purposes to detect or quantify monocyte chemotactic proteins, and purification of monocyte chemotactic proteins. Therefore, kits comprising an antibody of the invention for any of the purposes described herein are also within the scope of the invention.

The β-chemokines, particularly MCP-1, MCP-2 and MCP-3 have been shown to play a role in pathological conditions associated with inflammation (Van Coillie et al. (1999) *Cytokine & Growth Factor Rev.* 10:61-86). MCP-1, MCP-2, and MCP-3 have all been shown to have potent chemotactic activity for leukocytes, especially monocytes (van Coillie et al. (1999) *Cytokine & Growth Factor Rev.* 10:61-86). All three chemokines also share other functions (e.g., glucosaminidase release, gelatinase B release, granzyme A) which combined with their chemotactic activity enable leukocytes to migrate into tissues and towards sites of inflammation. Recruitment of leukocytes to inflammatory sites is thought to contribute greatly to the inflammatory process. Inhibition of leukocyte recruitment via MCP-1 antagonism (e.g., in MCP-1 knockout animals and in MCP-1 depletion studies using anti-MCP-1 mAbs) has been shown to reduce leukocyte infiltration (particularly monocyte recruitment) and is correlated with reduction in disease (van Coillie et al. (1999) *Cytokine & Growth Factor Rev.* 10:61-86).

Like MCP-1, MCP-2 and MCP-3 are also molecules with potent chemotactic activity for monocytes, T lymphocytes, and basophils. Given their overlapping activities and the increased expression of all three chemokines (MCP-1, MCP-2, and MCP-3) in human disease, blockade of all three MCP molecules is expected to have a greater beneficial effect than just inhibition of MCP-1 alone. Blockade of multiple MCP molecules (MCP-1, MCP-2 and MCP-3) should more efficiently inhibit recruitment of certain cell types for which MCP-1 is a poor chemotactic stimulus. Thus, while MCP-1 does not efficiently induce migration of eosinophils or resting neutrophils, MCP-2 is a potent chemotactic stimulus for eosinophils, and MCP-3 shows activity against both eosinophils and neutrophils (van Coillie et al. (1999) *Cytokine & Growth Factor Rev.* 10:61-86).

Accordingly, the antibodies and antibody fragments of the invention are useful to modulate the activity of these chemokines and affect the pathology of disorders associated with these chemokines. As such, these antibodies and fragments are useful, in therapeutic compositions for the treatment of inflammatory conditions and pathological conditions associated with expression of MCP molecules. In these embodiments, a patient is identified as having one of the diseases to be treated, such as by exhibiting at least one sign or symptom of the disease or disorder. At least one antibody or antigen-binding fragment thereof of the invention or compositions comprising at least one antibody or antigen-binding fragment thereof of the invention is administered in a sufficient amount to alleviate at least one symptom of the disease or disorder, or to reduce the activity of at least one of MCP-1, MCP-2 or MCP-3.

Disorders Amenable to Prevention or Treatment

As used herein, the terms "a disorder in which MCP activity is detrimental" and "an MCP-associated disorder" are intended to include diseases and other disorders in which the presence of MCP, including MCP-1, MCP-2, and/or MCP-3, in a subject suffering from the disorder has been shown to be or is suspected of being either responsible for the pathophysiology of the disorder or a factor that contributes the disorder. Accordingly, a disorder in which MCP activity is detrimental is a disorder in which inhibition of MCP activity is expected to prevent or alleviate the symptoms and/or progression of the disorder. Such disorders may be evidenced, for example, by an increase in the concentration of MCP in a biological fluid of a subject suffering from the disorder (e.g., an increase in the concentration of MCP-1 in serum, plasma, synovial fluid, urine, etc. of the subject), which can be detected, for example, using an anti-MCP antibody as described above. There are numerous examples of disorders in which MCP activity is detrimental. The use of the antibodies and antibody portions of the invention in the prevention or treatment of specific disorders is discussed further below.

Fibrotic Disease

In one embodiment of the invention, an antibody or antigen-binding fragment thereof, having binding specificity for MCP-1, MCP-2 and/or MCP-3, e.g., an antibody or antigen-binding fragment comprising CDRs from either the 1A1 or 11K2 antibodies, is used in a method of prevention or treatment of a patient suffering from a fibrotic disease. A "fibrotic disease" as used herein includes any condition marked by an increase of interstitial fibrous tissue. MCPs are known to be associated with fibrotic conditions. For example, MCP-1 is a potent chemoattractant for monocytes and has been implicated in a variety of inflammatory and fibrotic diseases, the pathogenesis of which is known to involve infiltration and activation of monocytes (Mang, et al (1994) *J. Immunol.* 153:4733-4741). Along with increased TGF-β and collagen production, fibrotic diseases are also characterized by increased levels of MCP-1 (Antoniades et al. (1992) *J. Immunol.* 89:5371-5375; Wada et al. (1996) *FASEB J.,* 10:1418-1425; Saitoh et al. (1998) *J. Clin. Lab. Anal.* 12:1-5; Hasegawa et al. (1999) *Clin. Exp. Immunol.* 117:159-165; Wada et al. (1999) *Kidney Int.* 65:995-1003; Wada et al. (2000) *Kidney Int.* 58-1492-1499). Increased expression of MCP-1 during fibrotic diseases has been well characterized in both human and in rodent models. In humans, MCP-1 is up-regulated in idiopathic pulmonary fibrosis (Antoniades et al., supra), IgA nephropathy (Saitoh et al., supra), diabetic nephropathy (Wada et al. (2000), supra), lupus nephritis (Wada et al. (1996), supra), crescentic glomerulonephritis (Wada, 1999), supra), and scleroderma (Hasegawa, supra). While not expressed in normal tissues, MCP-1 was highly expressed in the fibrotic skin and lungs of scleroderma patients, and the elevated levels of MCP-1 found in patient serum correlated with the presence of fibrosis and with earlier onset of scleroderma (Hasegawa, supra). MCP-1 expression also correlated positively with severity of renal fibrosis in diseases such as IgA nephropathy, diabetic nephropathy, lupus nephritis, and crescentic glomerulonephritis.

Oncogenic Disease

In another embodiment of the invention, an antibody or antigen-binding fragment thereof, having binding specificity for MCP-1, MCP-2 and/or MCP-3, e.g., an antibody or antigen-binding fragment comprising CDRs from either the 1A1 or 11K2 antibodies, is used in a method of prevention or treatment of a patient suffering from an oncogenic disease or cancer. MCPs are known to be associated with oncogenic conditions. For example, MCP-1 is a potent inducer of angiogenesis and plays an important role in tumor growth. Evidence for a role of MCP-1 in tumorigenesis involved treatment of immunodeficient mice bearing MCP-1 producing human breast carcinoma cells with neutralizing anti-MCP-1 mAb (Salcedo, (2000) *Blood* 96:34-40). Treatment with anti-MCP-1 mAb resulted in significant increases in animal survival (mean survival increased from 45 days to 75 days) and marked inhibition of tumor metastasis (60% decrease in lung metastatic index).

Immunopathologic Disease

In another embodiment of the invention, an antibody or antigen-binding fragment thereof, having binding specificity for MCP-1, MCP-2 and/or MCP-3, e.g., an antibody or antigen-binding fragment comprising CDRs from either the 1A1 or 11K2 antibodies, is used in a method of prevention or treatment of a patient suffering from an immunopathologic disease. An "immunopathologic disease" as used herein is defined as any condition associated with an immune response which is related to a disease. MCPs have been associated with immunopathologic conditions. For example, there is a strong link between MCP-1 expression and immunopathologic disease in humans. Experiments mine genetically-engineered mice and in vivo data using function-blocking antibodies to MCP-1 provide evidence supporting the validity of MCP-1 antagonism in a variety of diseases characterized by mononuclear infiltration. Included among these diseases is: atherosclerosis (MCP-1 KO, CCR2 KO), arthritis (MCP-1 mAb), asthma (MCP-1 mAb), glomerulonephritis (MCP-1 KO, MCP-1 mAb), lupus nephritis (MCP-1 KO) and multiple sclerosis (MCP-1 KO, MCP-1 mAb, CCR2KO) (see, for example, Lu et al. (1998) *J. Exp. Med.* 187601-608); Kurihara et al. (1997) *J. Exp. Med.* 186; 1757-1762; Boring et al. (1997) *J. Chin. Invest.* 100:2552-2561); Kuziel et al. (1997) *PNAS* 94:12053-12058; Blease et al. (2000) *J. Immunol.* 165: 2603-2611; Traynor et al. (2000) *J. Immunol.* 164; 2021-2027; Boring et al. (1998) *Nature* 394:894-897; Dawson et al. (1999) *Atherosclerosis* 143:205-211; Fife et al. (2000) *J. Exp. Med.* 192: 899-905; Izikson et al. (2000) *J. Exp. Med.* 192: 1075-1080; Bird et al. (2000) *Kidney Int.* 57:129-136; MacLean et al. (2000) *J. Immunol.* 165:165:6568-6575; Karpus et al. (1997) *J. Leukoc. Biol.* 62:681-687; Gonzalo et al. (1998) *J. Exp. Mal.* 188:157-167). In all these cases, interference with the MCP-1 pathway resulted in dramatically reduced leukocyte infiltration, with monocyte recruitment being particularly affected. This dramatic reduction in monocyte recruitment correlated well with reduction in disease.

Other Disorders

In certain embodiments, the antibodies or antigen-binding fragments of the present invention are useful in the prevention or treatment of glomerulonephritis, scleroderma, cirrhosis, multiple sclerosis, lupus nephritis, atherosclerosis, inflammatory bowel diseases or rheumatoid arthritis. In another embodiment, the antibodies or antigen-binding fragments of the invention can be used to treat or prevent inflammatory disorders, including, but not limited to, Alzheimer's, severe asthma, atopic dermatitis, cachexia, CHF-ischemia, coronary restenosis, Crohn's disease, diabetic nephropathy, lymphoma, psoriasis, fibrosis/radiation-induced, juvenile arthritis, stroke, inflammation of the brain or central nervous system caused by trauma, and ulcerative colitis. Other inflammatory disorders which can be prevented or treated with the antibodies or antigen-binding fragments of the invention include inflammation due to corneal transplantation, chronic obstructive pulmonary, disease, hepatitis C, multiple myeloma, and osteoarthritis. In another embodiment, the antibodies or antigen-binding fragments of the invention can be used to prevent or treat neoplasia, including, but not limited to bladder cancer, breast cancer, head and neck cancer, kaposi's sarcoma, melanoma, ovarian cancer, small cell lung cancer, stomach cancer, leukemia/lymphoma, and multiple myeloma. Additional neoplasia conditions include, cervical cancer, colo-rectal cancer, endometrial cancer, kidney cancer, non-squamous cell lung cancer, and prostate cancer. In another embodiment, the antibodies or antigen-binding fragments of the invention can be used to prevent or treat fibrotic disorders, including, but not limited to CHF-ischemia, coronary restenosis, diabetic vasculopathy, myocardial infarction/unstable angina, and radiation fibrosis. Additional examples of fibrotic disorders which can be treated in accordance with the invention include diabetic nephropathy, and impotence (Peyronie's). In another embodiment, the antibodies or antigen-binding fragments of the invention can be used to prevent or treat neurodegenerative disorders, including, but not limited to Alzheimer, stroke, and traumatic brain or central nervous system injuries. Additional neurodegenerative disorders include ALS/motor neuron disease, diabetic peripheral neuropathy, diabetic retinopathy, Huntington's disease, macular degeneration, and Parkinson's disease.

In clinical applications, a patient is identified as having or at risk of developing a disease or disorder associated with detrimental MCP activity, such as by exhibiting at least one sign or symptom of the disease or disorder. At least one antibody or antigen-binding fragment thereof of the invention or compositions comprising at least one antibody or antigen-binding fragment thereof of the invention is administered in a sufficient amount to treat at least one symptom of the disease or disorder, or to reduce the activity of at least one of MCP-1, MCP-2 or MCP-3.

Moreover, an antibody of the invention can be administered to a non-human mammal expressing a chemokine with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Examples of animal models which can be used for evaluating the therapeutic efficacy of antibodies or antigen-binding fragments of the invention for preventing or treating glomerulonephritis include anti-GBM-induced glomerulonephritis (Wada et al. (1996) Kidney Int. 49:761-767) and anti-thy1-induced glomerulonephritis (Schneider et al. (1999) Kidney Int. 56:135-144). Examples of animal models which can be used for evaluating the therapeutic efficacy of antibodies or antigen-binding fragments of the invention for preventing or treating cirrhosis include carbon tetrachloride-induced cirrhosis and liver fibrosis (Sakadamis et al. (2001) Res Exp Med 200:137-54). Examples of animal models which can be used for evaluating the therapeutic efficacy of antibodies or antigen-binding fragments of the invention for preventing or treating multiple sclerosis include experimental autoimmune encephalomyelitis (EAE) (Link and Xiao (2001) Immunol. Rev. 184:117-128). Animal models can also be used for evaluating the therapeutic efficacy of antibodies or antigen-binding fragments of the invention for preventing or treating lupus, for example using the MRL-Fas$^{lpr}$ mice (Schneider, supra; Tesch et Ed. (1999) J. Exp. Med. 190). Examples of animal models which can be used for evaluating the therapeutic efficacy of antibodies or antigen-binding fragments of the invention for preventing or treating atherosclerosis include using mice deficient in apolipoprotein A, ApoE, and LDL $R_L$ (Dansky et al. (1999) Arterioscler Thromb. Vasc. Biol. 19:1960-1968; Lou et al. (1998) PNAS 95:12591-12595). Examples of animal models which can be used for evaluating the therapeutic efficacy of antibodies or antigen-binding fragments of the invention for preventing or treating inflammatory bowel disease (IBD) include TNBS-induced IBD, DSS-induced IBD, and (Padol et al. (2000) Eur. J. Gastrolenterol. Hepatol. 12:257; Murthy et al. (1993) Dig. Dis. Sci. 38:1722). Examples of animal models which can be used for evaluating the therapeutic efficacy of antibodies or antigen-binding fragments of the invention for preventing or treating rheumatoid arthritis (RA) include adjuvant-induced RA, collagen-induced RA, amd collagen mAb-induced RA (Holmdabl et al., (2001) Immunol. Rev. 184:184; Holmdahl et al, (2002) Ageing Res. Rev. 1:135; Van den Berg (2002) Curr. Rheumatol. Rep. 4:232).

In addition, animal models for evaluating the efficacy of antibodies or antigen-binding fragments of the invention in treating or preventing human fibrotic diseases, include rodent models of pulmonary (Brieland et al. (1992) Am. J. Respir. Cell. Mol. Biol 7:134-139; Mang et al. (1994) J. Immunol. 153:4733-4741; Johnston et al. (1998) Exp. Lung Res. 24:321-337), vascular (Furukawa et al. (1999) Circ. Res. 84:306-314), and renal (Lloyd et al. (1997) J. Exp. Med. 185:1371-1380; Fujinaka et al. (1997) J. Am. Soc. Nephrol. 8:1174-1178; Schneider, supra Tesch et al. (1999) J. Exp. Med. 190:1813-1824; Tesch et al. (1999) J. Clin. Invest. 103:73-80) fibrosis. Alport's model of renal fibrosis can also be used to evaluate the efficacy of the antibodies or antigen-binding fragments of the invention.

The therapeutic compositions of the invention include at least one antibody or antibody fragment of the invention in a pharmaceutically acceptable carrier. A "pharmaceutically acceptable carrier" refers to at least one component of a pharmaceutical preparation that is normally used for administration of active ingredients. As such, a carrier may contain any pharmaceutical excipient used in the art and any form of vehicle for administration. The compositions may be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like.

The therapeutic compositions of the invention may be administered by any acceptable route of administration including, but not limited to intravenous, intradermal, interperitoneal, enteric, vaginal, rectal, nasal, transdermal, subcutaneous, and intramuscular.

Methods for Screening of β-Chemokine Pan-Antibodies

The pan-antibodies and fragments thereof of the invention may be assayed for specific binding to the β-chemokines, particularly MCPs (e.g., MCP-1, MCP-2 and MCP-3) in competitive and non-competitive binding immunoassays. Well-known procedures for immunoassays may be found, for example, in Stites and Tar (Eds.) BASIC AND CLINICAL IMMUNOLOGY (7th ed.), 1991; Maggio (Ed.) ENZYME IMMUNOASSAY, CRC Press, Boca Raton, Fla., 1980; Tijan (1985); PRACTICE AND THEORY OF ENZYME IMMUNOASSAYS, LABORATORY TECHNIQUES IN BIOCHEMISTRY AND MOLECULAR BIOLOGY, Elsevier Science Publishers B. V., Amsterdam; Harlow and Lane (Eds.) ANTIBODIES, A LABORATORY MANUAL, Cold Spring Harbor, N.Y., 1988; Chan (Ed.) (1987) IMMUNOASSAY: A PRACTICAL GUIDE, Academic Press, Orlando, Fla., 1987; Price and Newman (Eds.) PRINCIPLES AND PRACTICE OF IMMUNOASSAYS, Stockton Press, N.Y. 1991; and Ngo (Ed.) (1988) NON-ISOTOPIC IMMUNOASSAYS, Plenum Press, 1988; the disclosures of which are incorporated by reference herein.

Immunoassays to measure antibody binding can be either competitive or noncompetitive. In general in the antibody context, a competitive assay involves competition for binding of a ligand between two antibodies. For example, a labeled MCP-1 may be used to assess whether one antibody can compete with another antibody for binding the labeled MCP-1. The assay may be based on such standard assays as the enzyme linked immunosorbent assay (ELISA) or radioimmunoassay (RIA) for example.

Alternatively, the antibodies and antibody fragments of the invention may be tested in noncompetitive assays for binding to substrates. For instance, a standard ELISA may be used in which the ligand (e.g., MCP-1) is immobilized on an ELISA plate. A test antibody is incubated with the ligand and allowed to bind. The plate is washed and thereafter, an enzyme-conjugated, secondary antibody (e.g., a mouse anti-human Fc antibody) binds to the test antibody if the test antibody is bound to the ligand. After washing, a substrate for the enzyme is added and allowed to react with the enzyme. Generally a color change indicates the presence of an antibody that reacts with the ligand. The ELISA may be repeated for different β-chemokines to determine which chemokines are recognized by the test antibody.

Immunoassays often use labeled assay components. The label can be in a variety of forms and may be coupled directly or indirectly to the desired component of the assay according to methods well known in the art. Common labels for assay components include radioactive isotopes, including $^3H$, $^{125}I$, $^{35}S$, $^{14}C$, and $^{32}P$, fluorophores, chemiluminescent agents, and enzymes. The choice of a particular label will depend on the sensitivity required, the ease of conjugation with the compound, the stability requirements, and the available instrumentation, and will be easily determined by one of ordinary skill in the art.

In order to determine that the monoclonal antibodies do not bind the MRHAS motifs, an ELISA for MRHAS family members, such as regions of rubella structural proteins, HIV gag, HIV envelope, *Haemophilus influenzae* lipoprotein *Neisseria menigitidis* POPM3, *Streptococcus pneumoniae* Protein A, and *Listeria monocytogenes* protein precursor, as shown in WO 95/09232. Those antibodies that bind to a non-chemokine MHRAS member are not antibodies of the invention.

An example of a screening assay is set forth in the Examples, but the invention is not limited thereto or thereby.

Assays to assess whether the antibodies of the invention inhibit fit-chemokine activity, particularly MCP activity (e.g., MCP-1, MCP-2 and MCP-3 activity) may be easily performed using known assays for chemotaxis, intracellular calcium increase, and the like.

For example, but not by way of limitation, chemokine chemotaxis assays may be performed in 48 well plastic chambers. The wells are separated by a filter into two compartments. The filter allows the passage of cells from one compartment to the next in response to chemical gradients. Test cells are placed in one compartment of the chamber in a culture medium and an MCP, for example, is placed in culture medium in the other compartment. Cells adhering to the filter or traversing the filter are counted. In other wells, the MCP is mixed with the test antibody to determine if the antibody is able to block cell migration.

In Vitro Assays

The antibodies and antibody fragments of the invention may be used to detect MCPs in samples using a variety of well-known immunological assays. The antibodies may be used, for example, in ELISAs, Western blots, radioimmunoassays, immunoprecipitaton, immunoaffinity chromatography, immunostaining of tissue sections, immunogold detection in tissue samples with electron microscopy, and the like. The protocols for these and other assays are well-known in the art and are well within the purview of the skilled artisan.

The immunoassays using the antibodies and antibody fragments of the invention may be used to detect the presence and relative amounts of fit-chemokines in a sample. Samples may include, but are not limited to, homogenized tissue or cells, histological tissue sections for light and electron microscopy, protein extracts of tissue or cells, serum, blood, and the like. The presence of increased amounts of a β-chemokine(s) relative to normal samples, for example, may indicate the presence of a disease state, and treatment with a therapeutic of the invention may be indicated. In some instances, there may be a decreased amount of β-chemokine(s) relative to normal samples, and treatment with appropriate β-chemokine(s) or internal image antibodies that mimic β-chemokine(s) may be used to stimulate immune function.

In some embodiments, an immunoassay may be used to aid in the purification of β-chemokines. For example, an immunoaffinity resin may be used in which the antibodies or antibody fragments of the invention are immobilized on a substrate. A sample containing the β-chemokine(s) is added to the immunoaffinity resin and the antibodies become bound to the resin, while other components of the sample remain in solution. The resin is washed and the β-chemokines are subsequently eluted from the resin, substantially purified and isolated. Preferably, the antibodies used in the immunoassay will have high binding affinity, as defined herein.

This invention is further illustrated by the following examples which should not be construed as limiting. The contents of all references, patents and published patent applications cited throughout this application, as well as the figures and the Sequence Listing, are incorporated herein by reference.

EXAMPLES

I. Characterization of Anti-Chemokine Monoclonal Antibody Supernatants

Example 1

ELISA Screening

MaxiSorp 384 well plates were coated with 15-20 µl antigen in PBS. Recombinant purified human antigens included: MCP-1, MCP-2, MCP-3, MCP-4, IL-8, eotaxin, fractalkine, Gcp-2, DC-CK (Gcp-2 and DC-CK are also chemokines). Plates were incubated with antigen for 2 hours at 37° C. or overnight at 4° C. Non-specific sites were blocked with 80 µl/well of 1% BSA/PBS for 1 hour at room temperature. Plates were washed and 15 µl of hybridoma supernatant was added to each well and incubated for 1 hour at room temperature. Plates were washed and wells were incubated with 20 µl/well of a 1:25 000 dilution of goat anti-mouse IgG peroxidase conjugate (Jackson Catalog Number 515-036-003). Plates were incubated for 1 hour at room temperature, washed, and 20 µl/well of substrate (TMB, tetramethylbenzidine, Jackson, Catalog Number 515-036-062) was added. Reaction was allowed to proceed and stopped by addition of 20 µl/well of 2M $H_2SO_4$. Reactive clones were picked for further analysis. Isotyping of hybridoma supernatants was performed by antigen-dependent ELISA. Briefly, wells were coated with 50 µl of human MCP-1 (5 µg/ml) for 1 hour at 37° C. Wells were washed 4 times and blocked with PBS/1% BSA. Isotyping of hybridoma supernatants was then performed using a mouse immunoglobulin screening/isotyping kit (Zymed Laboratories, San Francisco, Calif.) as recommended by the manufacturer. Specificities of the antibodies and clones obtained are shown in Table 1.

TABLE 1

| Panel of MCP mAbs | | | | | | | | | |
|---|---|---|---|---|---|---|---|---|---|
| | | | Specificity | | | | | | Block |
| Fusion | Immunogen | Clone | MCP-1 | MCP-2 | MCP-3 | MCP-4/IL-8/Eotaxin/Frac Gcp-2/DC-CK | Affinity (Biacore) | Sub-Type | MCP-1 ligand binding |
| IA1 | MCP-1 | 1M-11 | ++++ | – | – | – | ++++ | IgG1 | ++++ |
| | | 3N10 | ++++ | – | – | – | ++++ | IgG1 | ++++ |
| IA7 | MCP-1 | 11K2 | ++++ | ++++ | ++++ | – | ++++ | IgG1 | ++++ |

TABLE 1-continued

Panel of MCP mAbs

| Fusion | Immunogen | Clone | Specificity | | | | Affinity (Biacore) | Sub-Type | Block MCP-1 ligand binding |
|---|---|---|---|---|---|---|---|---|---|
| | | | MCP-1 | MCP-2 | MCP-3 | MCP-4/IL-8/Eotaxin/Frac Gcp-2/DC-CK | | | |
| | MCP-2 | 7F7 | ++++ | – | – | – | ++++ | IgG1 | +++ |
| | MCP-3 | 6D21 | ++++ | ++++ | ++ | – | ++++ | IgG1 | ++++ |
| | | 6E11 | ++ | – | + | – | +++ | IgM | +++ |
| | | 1A1 | +++ | + | + | – | ++++ | IgG1 | ++++ |
| IA8 | MCP-1 | 4N4 | ++++ | ++ | ++ | – | ++++ | IgG1 | ++++ |
| | MCP-2 | 5A13 | +++ | ++ | ++ | – | +++ | IgG1 | ++++ |
| IA9 | MCP-1 | 5J23 | ++++ | ++ | – | – | ++++ | IgG1 | ++++ |
| | MCP-2 | 6I5 | ++++ | +++ | +++ | – | ++++ | IgG1 | ++++ |
| | MCP-3 | 7H1 | ++++ | ++++ | ++++ | – | ++++ | IgG1 | ++++ |
| IA10 | MCP-1 | 4N9 | + | – | ++ | – | ++++ | IgG1 | +++ |
| | MCP-2 | 2O24 | ++ | – | ++ | – | ++++ | IgG1 | +++ |
| | MCP-3 | 9H23 | ++ | – | + | – | +++ | IgG1 | +++ |
| | | 9B11 | ++++ | – | ++++ | – | ++++ | IgG1 | +++ |
| | | 9B12 | + | – | +++ | – | ++++ | IgG1 | +++ |
| | | 9C11 | ++++ | – | ++++ | – | ++++ | IgG1 | +++ |
| | | 10D18 | ++++ | – | ++++ | – | ++++ | IgG1 | ++++ |
| | | 12F15 | +++ | – | +++ | – | ++++ | IgG1 | ++++ |
| | MCP-1 | D9 | ++++ | – | – | – (MCP-4, IL-8 and eotaxin only tested) | | | +++ |

+ and – indicate the relative amount of binding of the antibody to the various immobilized ligands.

In addition, both 1A1 and 11K2 mAbs recognize primate MCP-1. Plates were coated with 1 µg/ml of chemically synthesized chemokines (corresponding to the cynomolgus and rhesus MCP-1 sequences) and probed with 10 µg/ml of monoclonal antibodies, including MOPC21, 11K2, 3N10, 1A1, D9, and 1M11, as described above. Results demonstrate that all of the above mAbs, including 1A1 and 11K2, and with the exception of the isotype control mAb MOPC21, also recognize primate MCP-1.

Example 2

Binding Assay $^{125}$I labeled MCP-1 (2200 Ci/mmol) was purchased from NEN Life Sciences (Boston, Mass.). Hybridoma supernatants (50 µl) were pre-incubated with 1 nM $^{125}$I MCP-1 (50 µl) for 60 minutes at room temperature prior to the addition of the CCR2-expressing human monocyte cell line, THP-1. THP-1 cells (1×10$^7$ cells/ml; 50 µl) were resuspended in binding buffer (50 mM Hepes, 1 mM CaCl$_2$, 5 mM MgCl$_2$, 0.5% BSA) and added to the combination of $^{125}$I labeled MCP-1 and hybridoma supernatant, and incubated at 4° C. for 60 minutes. Cells were then washed 3 times by centrifugation in wash buffer (50 mM Hepes, 1 mM CaCl$_2$, 5 mM MgCl$_2$, 500 mM NaCl and 0.5% BSA). Amount of bound $^{125}$I labeled MCP-1 was then quantitated for γ-emission. Pre-incubation of THP-1 cells (1×10$^7$ cells/ml; 50 µl) with unlabeled MCP-1 (500 nM; 50 µl) for 60 minutes at 4° C. prior to addition of $^{125}$I labeled MCP-1 (1 nM; 50 µl) served as a negative control. The positive control represents binding of $^{125}$I labeled MCP-1 to THP-1 cells in the absence of MCP-1 hybridoma supernatant. The results are shown in Table 2.

TABLE 2

Data of block ligand ([I$^{125}$] MCP-1) binding assay from γ Counter

| Fusion | Immunogen | Clone # | CPM (30/10/00) | | CPM (22/11/00) | |
|---|---|---|---|---|---|---|
| IA1 | MCP-1 | 1M-11 | 499 | 456 | 45 | 40 |
| | | 3N10 | 379 | 495 | 50 | 46 |
| IA7 | MCP-1 | 11K2 | 103 | 148 | 50 | 49 |
| | MCP-2 | 7F7 | 394 | 199 | 189 | 197 |
| | MCP-3 | 6D21 | 145 | 108 | 47 | 42 |
| | | 6E11 | 850 | 894 | 378 | 323 |
| | | 1A1 | 194 | 772 | 47 | 52 |
| IA8 | MCP-1 | 4N4 | | | 40 | 47 |
| | MCP-2 | 5A13 | | | 50 | 44 |
| IA9 | MCP-1 | 5J23 | 478 | 280 | 59 | 47 |
| | MCP-2 | 6I5 | 677 | 678 | 44 | 31 |
| | MCP-3 | 7H1 | 53 | 207 | 59 | 77 |
| IA10 | MCP-1 | 4N9 | 776 | 987 | 306 | 340 |
| | MCP-2 | 2O24 | 936 | 869 | 226 | 357 |
| | MCP-3 | 9H23 | | | 293 | 226 |
| | | 9B11 | 679 | 892 | 238 | 201 |
| | | 9B12 | 834 | 657 | 304 | 265 |
| | | 9C11 | 605 | 512 | 241 | 252 |
| | | 10D18 | 485 | 444 | 174 | 310 |
| | | 12F15 | 421 | 344 | 281 | 213 |
| | | 12K14 | | | 406 | 918 |
| Negative control | | | 836 | 461 | 68 | 143 |
| Positive control | | | 5861 | 3447 | 2084 | 2933 |

Example 3

Inhibition of Chemotaxis in Response to MCP-1

A 5 µm pore size ChemoTX plate (Neuroprobe) was used to assess the chemotactic response of THP-1 human monocytic cells. Hybridoma supernatants containing MCP-1 at 10 ng/ml, or RPMI with 10% FBS with or without 10 ng/ml chemokine, was added to the lower chamber of the plate. THP-1 cells at 2×10$^6$ cells/ml were layered on top. The plate was incubated for 2 hours at 37° C. in 5% CO$_2$. The filter was removed and the number of cells that migrated into the lower chamber was determined using Promega Cell Titer reagent.

The number of cells was calculated using a standard curve (n=4, error bars=standard deviation). The results are shown in FIG. 1. FIG. 1 shows that antibodies 11K2, 7F7, 6D21, and 7H1 were all able to inhibit MCP-1-induced chemotaxis, although 11K2 and 6D21 were the most effective.

II. Characterization of Purified Anti-Chemokine Monoclonal Antibodies

Example 4

Chemokine Specificity and Binding Assays

ELISA specificity assays were performed using purified monoclonal antibodies to confirm the binding specificities of the supernatant MCP-specific monoclonal antibodies described above. Antibodies were purified by Protein A affinity column chromatography, according to standard methods known in the art.

ELISA was performed as previously described in Example 1. Briefly, MaxiSorp 384 well plates were coated with 15-20 µl antigen in PBS. Recombinant purified human antigens included: MCP-1, MCP-2, MCP-3, MCP-4, IL-8, eotaxin, murine MCP-1 (JE), murine MCP-3, murine MCP-5, and rat MCP-1. All antigens, including MCP-3, were immobilized. Plates were washed and purified monoclonal antibody (10 µg/ml) was added to each well and incubated for 1 hour at room temperature. Plates were washed and wells were incubated with 20 µl/well of a 1:25,000 dilution of goat anti-mouse IgG peroxidase conjugate (Jackson Catalog Number 515-036-003). Plates were incubated for 1 hour at room temperature, washed, and 20 µl/well of substrate (TMB, tetramethylbenzidine, Jackson, Catalog Number 515-036-062) was added. Reaction was allowed to proceed and stopped by addition of 20 µl/well of 2M $H_2SO_4$. Specificities of the purified antibodies and are shown in Table 3. Antibodies 1A1 bound specifically to hMCP-1, hMCP-2, hMCP-3, and mMCP-1. Antibodies 11K2, 4N4, 5A13, 6D21, 6I5, and 7H1 bound specifically to hMCP-1, hMCP-2, hMCP-3, mMCP-1, mMCP-3, and mMCP-5.

Binding assays were performed using purified monoclonal antibodies to confirm results obtained with the supernatants. Binding assays were performed as described in Example 2. Briefly, $^{125}I$ labeled MCP-1 (2200 Ci/mol) was purchased from NEN Life Sciences (Boston, Mass.). Purified monoclonal antibodies at various concentrations (33 nM, 3.3 nM and 0.33 nM) were pre-incubated with 1 nM $^{125}I$ MCP-1 (50 µl) for 60 minutes at room temperature prior to addition of the CCR2-expressing human monocyte cell line, THP-1. THP-1 cells (1×10$^7$ cells/ml; 50 µl) were resuspended in binding buffer (50 mM Hepes, 1 mM $CaCl_2$, 5 mM $MgCl_2$, 03% BSA) and added to the combination of $^{125}I$ labeled MCP-1 and purified mAb, and incubated at 4° C. for 60 minutes. Cells were then washed 3 times by centrifugation in wash buffer (50 mM Hepes, 1 mM $CaCl_2$, 5 mM $MgCl_2$: 500 mM NaCl, and 0.5% BSA). Amount of bound $^{125}I$ labeled MCP-1 was then quantitated for γ-emission. Results from the binding assays are shown in Table 4. This study demonstrates that many of the studied monoclonal antibodies, including 1A1 and 11K2, were effective at blocking hMCP-1 binding.

TABLE 4

Purified mAb binding assay

| Antibody | Block hMCP-1 cell binding |
| --- | --- |
| 1A1 | + |
| 4N4 | + |
| 5A13 | + |
| 6D21 | + |
| 6I5 | + |
| 7H1 | + |
| 11K2 | + |
| D9 | + |
| 1M11 | + |
| 3N10 | + |
| 2O24 | − |
| 9B11 | − |
| 9B12 | − |
| 9C11 | − |
| 5J23 | + |

Example 5

Inhibition of Monocyte Chemotaxis by Anti-Chemokine Monoclonal Antibodies

A. MCP-1 and MCP-2 Chemotaxis Assay

A 5 µm pore size ChemoTX plate (Neuroprobe) was used to assess the chemotactic response of THP-1 human monocytic cells. Purified monoclonal antibodies (100 µg/ml) 11K2, 1A1, D9, and 2O24 were added in combination with and without MCP-1 (2.3 nM), MCP-2 (56 nM), and MCP-1/

TABLE 3

ELISA performed using purified MCP mAbs

| | hMCP-1 | hMCP-2 | hMCP-3 | hMCP-4 | mMCP-1 (JE) | mMCP-3 | mMCP-5 | rtMCP-1 | hIL8 | hEotaxin |
| --- | --- | --- | --- | --- | --- | --- | --- | --- | --- | --- |
| 1A1 | + | + | + | − | + | − | − | − | − | − |
| 4N4 | + | + | + | − | + | + | + | − | − | − |
| 5A13 | + | + | + | − | + | + | + | − | − | − |
| 6D21 | + | + | + | − | + | + | + | − | − | − |
| 6I5 | + | + | + | − | + | + | + | − | − | − |
| 7H1 | + | + | + | − | + | + | + | − | − | − |
| 11K2 | + | + | + | − | + | + | + | − | − | − |
| D9 | + | − | − | − | − | − | − | − | − | − |
| 1M11 | + | − | − | − | − | ND | ND | ND | ND | ND |
| 3N10 | + | − | − | − | − | ND | ND | ND | ND | ND |
| 2O24 | + | − | + | − | − | ND | ND | ND | ND | ND |
| 9B11 | + | − | + | − | − | ND | ND | ND | ND | ND |
| 9B12 | + | − | + | − | − | ND | ND | ND | ND | ND |
| 9C11 | + | − | + | − | − | ND | ND | ND | ND | ND |
| 5J23 | + | + | +/− | − | + | ND | ND | − | − | − |

MCP-2 (2.3 nM MCP-1 and 56 nM MCP-2), to the lower chamber of the plate. THP-1 cells at $2\times10^6$ cells/ml were layered on top. The plate was incubated for 4 hours at 37° C. in 5% $CO_2$. The filter was removed and the number of cells that migrated into the lower chamber was determined using Promega Cell Titer reagent.

Figure 2:
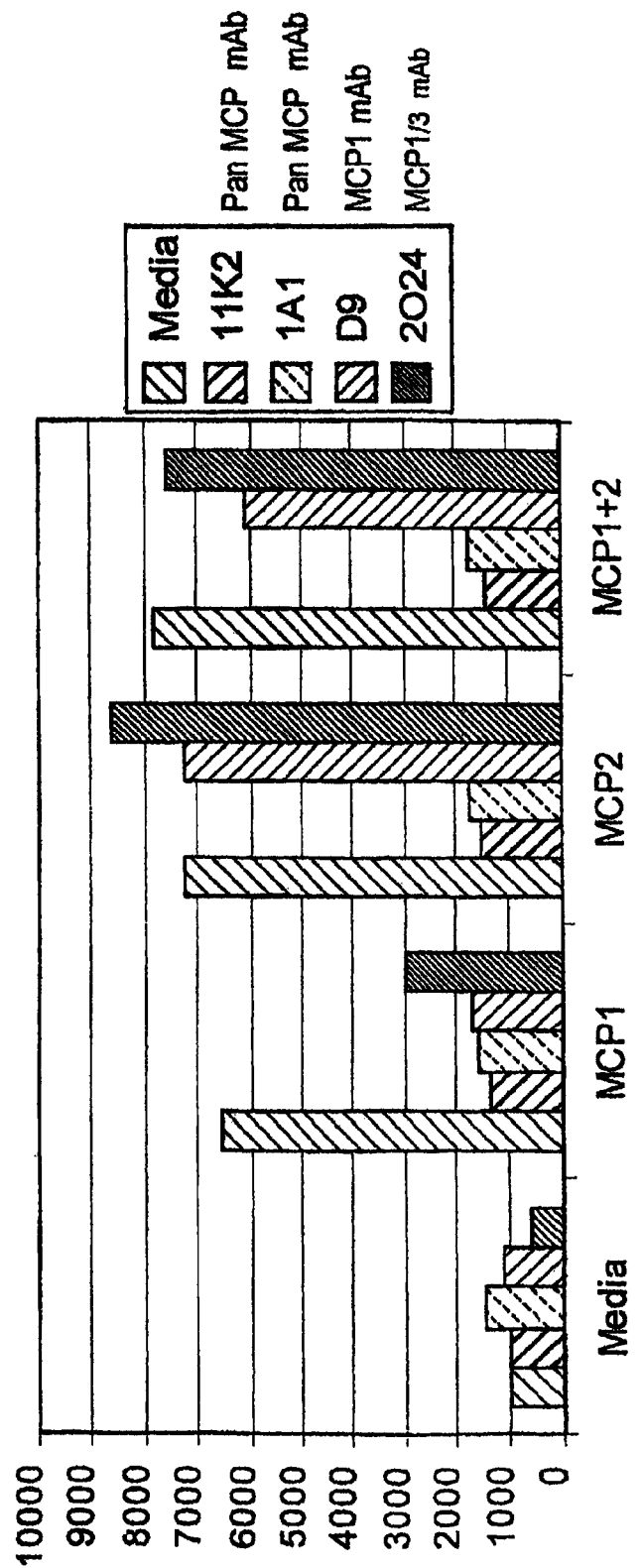
FIG. 2 graphically depicts results of a chemotaxis assay using purified 11K2, 1A1, D9, and 2O24 to inhibit chemotaxis in response to MCP-1, MCP-2, and a combination of MCP-1/MCP-2. The results show that chemotaxis to a combination of MCP-1 and MCP-2 is inhibited by 11K2 and 1A1.

The results show that pan-monoclonal antibodies 11K2 and 1A1 were effective at inhibiting chemotaxis in the presence of both MCP-1 and MCP-2 (FIG. 2). The results also demonstrate that antibodies D9 and 2O24 can inhibit chemotaxis which is induced by MCP-1 alone. Furthermore, as shown in FIG. 3, antibodies 1M11 and 3N10 can inhibit THP-1 chemotaxis induced by human MCP-1, and antibody 5J23 can inhibit chemotaxis induced by human and mouse MCP-1. In sum, chemotaxis to the combination of MCP-1 and MCP-2 is inhibited by 11K2 and 1A1, but is not observed by antibodies D9 and 2O24, which are MCP-1-specific mAb (D9 and 2O24).

Within the pool of monoclonal antibodies studied, there are three groups which arise based on their ability to recognize certain MCP antigens. Monoclonal antibodies 1A1 and 11K2 recognize MCP-1, MCP-2 and immobilized MCP-3. Monoclonal antibodies 1M11 and 3N10 recognize MCP-1, and antibody 2O24 recognizes MCP-1 and MCP-3. Antibody 5J23 recognizes mouse MCP-1 and recognizes only human MCP-1 and human MCP-2.

Results from a separate experiment using the ChemoTX plate (Neuroprobe) assay are shown below in Table 5. The protocol for this experiment was the same as previously described, except a titration of mAb was used in combination with fixed MCP concentrations (concentrations of MCPs are shown below in Table 5). The results described in Table 5 demonstrate that mAbs 11K2 and 1A1 are effective at inhibiting huMCP-1, huMCP-2, muMCP-1, and muMCP-5-induced chemotaxis.

chemokines was performed. RA fibroblasts were exposed for 48 hours to 500 U/ml IFN-γ, IFN-γ and 10 ng/ml of IL1β, or media (as a control). Results showed that IFN-γ alone induced low levels of MCP-1, MCP-2, MCP-3, and very low levels of IP10. IFN-γ exposure alone did not induce expression of Rantes, IL-8, Mip1α, or Mip1β. In contrast, the combination of IFN-γ and 10 ng/ml of IL1l3 induced about 27 ng/ml of MCP-1, 31 ng/ml of MCP-2, 9 ng/ml of MCP-3, and 55 ng/ml of IL-8. The combination of IFN-γ and 10 ng/ml of IL1β also yielded low levels of Rantes, IP10, and Mip1α. The media alone control did not induce any chemokine secretion.

Figure 4:
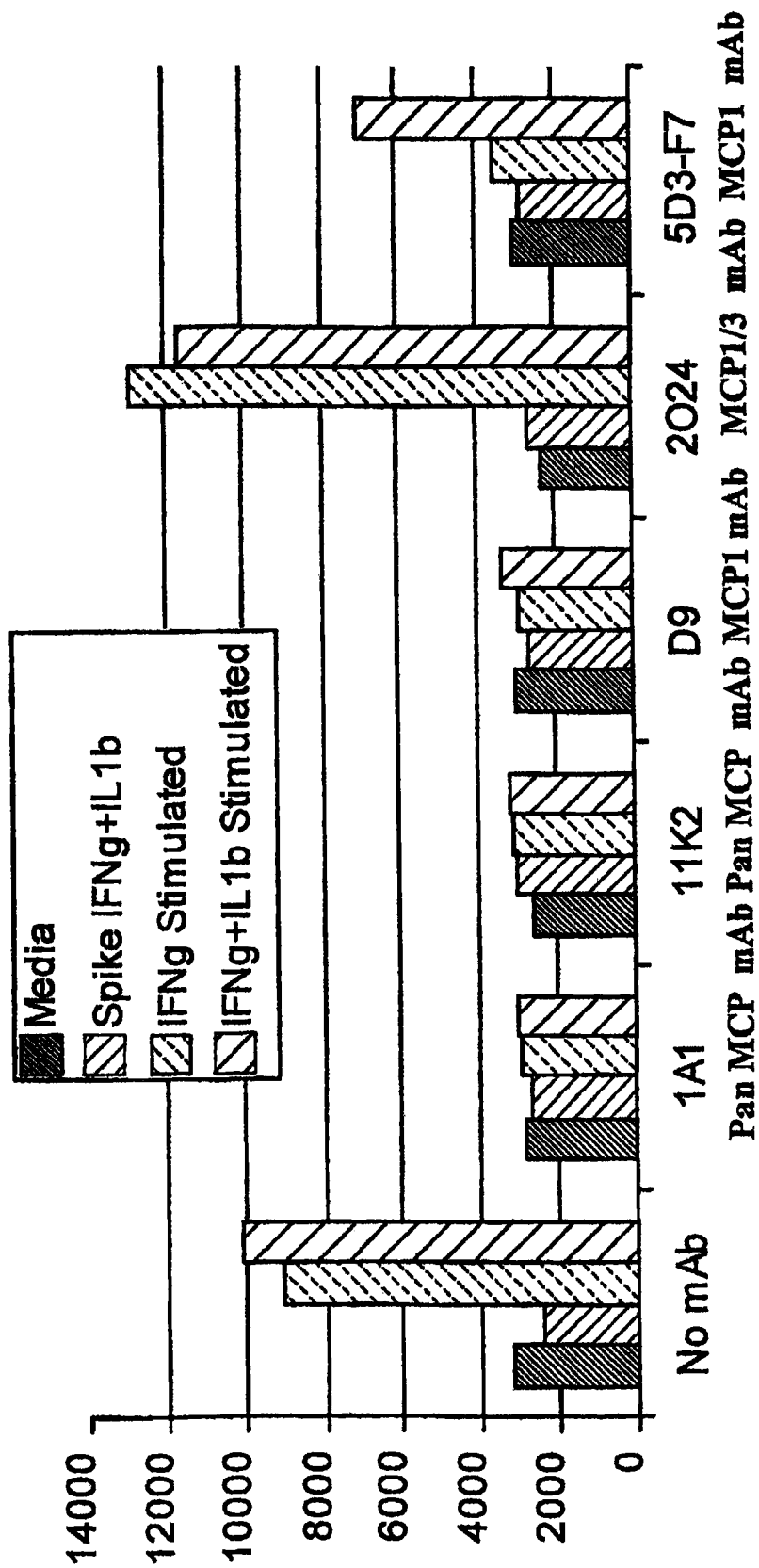
FIG. 4 graphically depicts results of a chemotaxis assay which demonstrates that monocyte chemotaxis mediated by cytokines secreted from stimulated rheumatoid arthritis (RA) fibroblasts is inhibited by pan-MCP mAbs (1A1 and 11K2) and MCP-1 mAb D9.

The ability of purified monoclonal antibodies to inhibit monocyte chemotaxis to cytokines secreted from these stimulated RA fibroblasts was then studied. Supernatant from RA fibroblasts which were exposed to either media alone, IFN-γ alone, or the combination of IFN-γ and IL-1β, were each tested for their chemotactic ability using human THP-1 cells. As a control, supernatant from unstimulated RA fibroblasts into which IFN-γ (500 U/ml) and IL1β (10 ng/ml) was spiked was used. This supernatant (spike) control was used to evaluate the direct effects of IL1β and IFN-γ on chemotaxis. As shown in FIG. 4, monocyte chemotaxis mediated by cytokines secreted from stimulated RA fibroblasts was inhibited by MCP mAbs 1A1 and 11K2. MCP-1-specific antibody D9 was also effective at inhibiting chemotaxis in all experimental groups.

Example 6

MCP-1-Induced Calcium Flux Assay for Monoclonal 11K2

The MCP-1-induced calcium flux assay was performed according to standard procedure. Briefly, monoclonal anti-

TABLE 5

11K2 and 1A1 inhibit THP-1 chemotaxis towards human MCP-1, human MCP-2, mouse MCP-1 and mouse MCP-5

| Human | | | | |
|---|---|---|---|---|
| $ND_{50}$ (nM) | MCP-1 (2.3 nM) | MCP-2 (56 nM) | MCP-3 (11.8 nM) | MCP-4 (58 nM) |
| Commercial | 10.0 | 33.0 | 2.6 | 11.5 |
| 1A1 | 1.4 | 47.5 | No Inhib | No Inhib |
| 11K2 | 1.3 | 52.0 | No Inhib | No Inhib |
| D9 | 5.8 | No Inhib | No Inhib | No Inhib |
| 2O24 | 1000.0 | No Inhib | 143.5 | No Inhib |

| Murine | | | | | |
|---|---|---|---|---|---|
| $ND_{50}$ (nM) | MCP-1 (1.4 nM) | MCP-2 | MCP-3 (59 nM) | MCP-4 | MCP-5 (0.54 nM) |
| Commercial | 3.2 | ND | 52.0 | ND | 0.1 |
| 1A1 | 1.7 | ND | No Inhib | ND | 13.5 |
| 11K2 | 2.1 | ND | No Inhib | ND | 19.5 |
| D9 | No Inhib | ND | No Inhib | ND | No Inhib |
| 2O24 | No Inhib | ND | No Inhib | ND | No Inhib |

No Inhib = less than 50% Neutralization at 3 uM

B. Inhibition of Chemotaxis by Cytokines Secreted from RA Fibroblasts

Figure 5A:
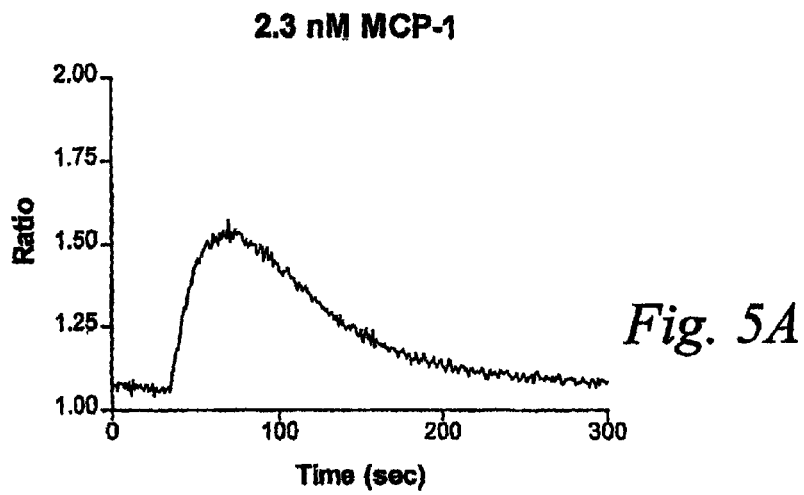
FIG. 5 graphically depicts results from a calcium flux assay using 11K2 (mAb and Fab fragments thereof) at various concentrations, including none (FIG. 5A), 20 nM mAb (FIG. 5B), and 60 nM Fab (FIG. 5C).
Figure 5B:
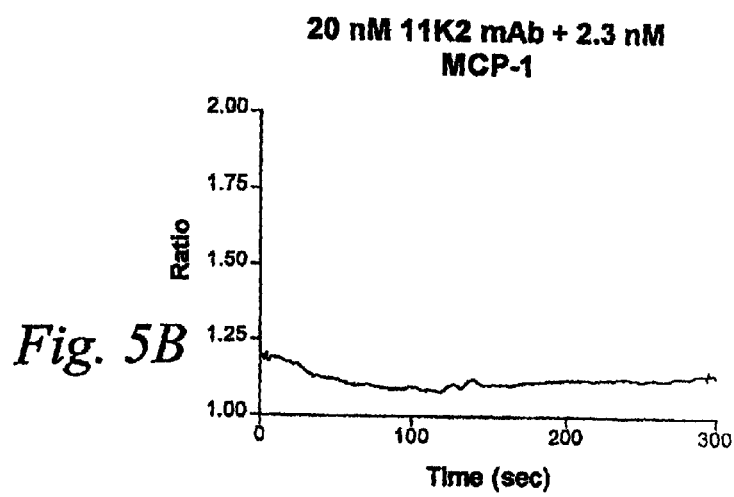
Figure 5C:
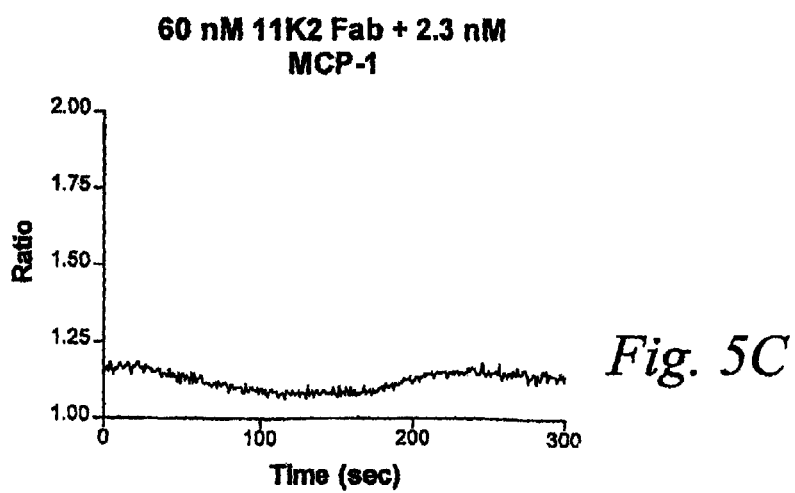

Prior to studying the ability of purified monoclonal antibodies 1A1, 11K2, D9, 2O24, and 5D3-F7 (BD Biosciences, Pharmingen, San Diego, Calif.), to inhibit chemotaxis from chemokines secreted from stimulated RA fibroblasts, a study of the different types of chemokines secreted by RA (rheumatoid arthritis) fibroblasts in response to inflammatory body 11K2 and a chemokine (MCP-1 or MCP-2) were mixed at 200× concentration and pre-incubated for one hour. This mixture was then added to THP-1 cells stirring in a cuvette in a fluorimeter at t=330 sec. Calcium flux was measured by a change in fluorescence of Indo-1. Results show that MCP-1-induced calcium flux in THP-1 cells was blocked by 11K2 (FIG. 5).

Example 7

Agonist Effect at Low Antibody Concentrations of 11K2 and 1A1

A. Chemotaxis Assay

Chemotaxis assays were performed as previously described with recombinant MCP-2 and using low concentrations of monoclonal antibodies 11K2 and 1A1. The results from the chemotaxis assay showed that at a low concentration, monoclonal antibodies 11K2 and 1A1 increased MCP-2 mediated chemotaxis. As shown in FIG. 6A, there was an increase in chemotaxis observed with low antibody concentrations (ranging from about 1-15 nM) of 11K2 and 1A1, in contrast to the MCP-2 mAb 281 (RD Systems, Minneapolis, Minn.). The agonist effect was not seen with the Fab fragment of 11K2 or 1A1, and was MCP-2-specific. As shown in FIG. 6B, low concentrations of the 11K2 Fab fragment did not result in a chemotactic increase in response to MCP-2 and showed only antagonist activity.

B. Calcium Flux Assay

A calcium flux assay was performed as previously described, except a low concentration of 11K2 monoclonal antibody (16.5 nM) was also included. The results (FIG. 7) demonstrate that low concentrations of 11K2 exposure results in agonistic activity in a MCP-2 calcium flux assay. In addition, however, 11K2 Fab and F(ab)2 fragments are inhibitory in the same assay (FIG. 7).

Example 8

Binding Affinity Measurement of Monoclonal 11K2 and 1A1

To measure the affinity of MCP mAb and Fab molecules for soluble MCP molecules, a kinetic exclusion assay was utilized and affinity measured using a KinExA instrument (Sapidyne Instruments Inc., Boise, Id.).

Polymethylmethacrylate beads activated with NHS were coated with 10 μg recombinant human MCP-1 in 1 ml buffer. The beads were packed into a column in the KinExA instrument for each sample. This packed bead column is able to capture free MCP mAb or Fab flowed through the column. The amount of free mAb or Fab in solution was determined using a secondary goat anti-mouse heavy and light chain IgG-Cy5 conjugate.

A fixed amount of 11K2 mAb, 1A1 mAb, 11K2 Fab, or 1A1 Fab was incubated with various amounts of human MCP-1, MCP-2 or MCP-3 for three hours. The amount of uncomplexed free antibody remaining in solution was determined by flowing these mixtures over the MCP-1-loaded bead column and labeling with the Cy5 secondary antibody. The fluorescent signal was plotted against the MCP concentration and the affinity was determined using a quadratic curve fit Affinities determined for both 11K2 and 1A1 mAb and Fab molecules are listed in Table 6 below. Exact affinities of 11K2 mAb and 1A1 mAb for human MCP-1 could not be determined, as the affinity is much lower than the lowest amount of antibody that can be detected by this method. In those cases, only an upper limit to the affinity can be determined. Affinity of the 11K2 Fab and 1A1 Fab for human MCP-3 was not determined (ND).

TABLE 6

| MCP binding affinity measurements in solution | | | |
|---|---|---|---|
| Antibody | MCP-1 | MCP-2 | MCP-3 |
| 11K2 mAb | $<4 \times 10^{-13}$ M | $1.8 \times 10^{-11}$ M | $>5 \times 10^{-8}$ M |
| 11K2 Fab | $1.1 \times 10^{-11}$ M | $4.3 \times 10^{-10}$ M | ND |
| 1A1 mAb | $<7 \times 10^{-13}$ M | $1.2 \times 10^{-12}$ M | $>5 \times 10^{-8}$ M |
| 1A1 Fab | $1.3 \times 10^{-11}$ M | $3.2 \times 10^{-10}$ M | ND |

In sum, monoclonal antibodies 1A1 and 11K2 recognize soluble human MCP-1 and MCP-2 with a very high binding affinity which is in the low pM range. Both 1A1 and 11K2 also recognize mouse MCP-1, while neither recognizes soluble MCP-3.

III. Cloning and Sequencing of 1A1 and 11K2 Monoclonal Antibodies

Example 9

Cloning and Sequencing of mu1A1 Variable Regions

Mouse monoclonal antibody 1A1 was cloned and sequenced according to the following procedure. Total cellular RNA from 1A1 murine hybridoma cells was prepared using the Qiagen RNeasy mini kit according to the manufacturer's recommended protocol.

cDNAs encoding the 1A1 variable regions of the heavy and light chains were cloned by RT-PCR from total cellular RNA, following standard procedures known to one of skill in the art. Briefly, following the manufacturer's recommended protocols, first-strand cDNAs (prepared with the Amersham First-Strand cDNA Synthesis Kit) were amplified by PCR using the Clontech Advantage 2 PCR Kit. The following primers were used for first-strand synthesis of the 1A1 heavy and light chain cDNAs (Y=C/T, and R=A/G): 1A1 Heavy Chain cDNA Primer: 5'-AGG TCT AGA AYC TCC ACA CAC AGG RRC CAG TGG ATA GAC-3' (SEQ ID NO:3) and 1A1 Light Chain cDNA Primer: 5'-GCG TCT AGA ACT GGA TGG TGG GAG ATG GA-3' (SEQ ID NO:4).

Primers used for PCR amplification of the murine 1A1 immunoglobulin heavy chain variable domain were as follows: 5'-AGG TSM ARC TGC AGS AGT CWG G-3' (SEQ ID NO:5) and 5'-TGA GGA GAC GGT GAC CGT GGT CCC TTG GCC CC-3' (SEQ ID NO:6) (S/G, M=A/C, R=A/G, and W=A/T). The primers used for PCR amplification of the murine 1A1 immunoglobulin light chain variable domain were: 5'-GAY ATH CAR ATG ACN CAG-3' (SEQ ID NO:7) and 5'-GCG TCT AGA ACT GGA TOG TGG GAG ATG GA-3' (SEQ ID NO:8) (Y=C/T, H=A/C/T, R=A/G, and N=A/C/G/T).

The PCR was performed at 30 cycles using Clontech's Advantage 2 PCR Kit using the following PCR conditions: denature 0.5 min at 94° C., anneal 1 min at 50° C., and elongate 1 min at 72° C. The PCR products were gel-purified using the Qiagen Qiaquick gel extraction kit following the manufacturer's recommended protocol. Purified 1A1 heavy and light chain PCR products were subcloned into Invitrogen's pCR2.1-TOPO vector using their TOPO TA Cloning kit according to the manufacturer's recommended protocol (pCR-049=1A1 heavy chain, per-053=1A1 light chain). Inserts from multiple independent subclones were sequenced according to methods known in the art and those described in Sanger et al., *PNAS* 74, 5463-5467, incorporated herein by reference, and subclones were found to be identical.

Sequence data was analyzed according to BLAST analysis (see http://www.ncbi.nlm.nih.gov). Blast analyses of the variable domain sequences confirmed their immunoglobulin identity. The 1A1 heavy chain variable domain was determined to be a member of murine subgroup II(C), while the 1A1 light chain variable region was determined to be a member of murine kappa subgroup II. The predicted amino acid sequences of the mature 1A1 murine variable domains, as well as the determined nucleotide sequences, are shown below in Tables 7 and 8.

TABLE 7

Nucleotide secnience of mu1A1 variable domains

1A1 Heavy Chain Variable Region
```
  1 GAGGTCCAGCTGCAGCAGTCTGGGGCAGAACTTGTGAGGTCAGGGGCCTCAGTCAAGTTG    60
 61 TCCTGCACAGCTTCTGGCTTCAACATTAAAGACAACTATATGCACTGGGTGAAGCAGAGG   120
121 CCTGAACAGGGCCTGGAGTGGATTGGATGGATTGATCCTGAGAATGGAGATACTGAATAT   180
181 GCCCCGAAGTTCCAGGGCAAGGCCACTATGACTGCAGACACATCCTCCAACACAGCCTAC   240
241 CTGCAGCTCAGCAGCCTGACATCTGAGGACACTGCCGTCTATTACTGTAATACATGGGCT   300
381 TACTACGGTACTAGCTACGGGGGATTTGCTTACTGGGGCCAAGGGACCACGGTCACCGTC   360
361 TCCTCA                                                         366
(SEQ ID NO: 9)
```

1A1 Light Chain Variable Region
```
  1 GATATCCAGATGACTCAGACTCCACTCACTTTGTCGGTTACCATTGGACAACCAGCCTCC    60
 61 ATCTCTTGCAAGTCAAGTCAGAGCCTCTTAGATAGTGATGGAAAGACATATTTGAATTGG   120
121 TCGTTACAGAGGCCAGGCCAGTCTCCAAAGCGCCTAATCTATCTGGTGTCTAAACTGGAC   180
181 TCTGGAGTCCCTGACAGGTTCACTGGCAGTGGATCAGGGACAGATTTCACACTGAAAATC   240
241 AGCAGAGTGGAGGCTGAGGATTTGGGAGTTTATTATTGCTGGCAAGGTACACATTTTCCT   300
301 CAGACGTTCGGTGGAGGCACCAAGCTGGAGATCAAA                           336
(SEQ ID NO: 10)
```

TABLE 8

Amino acid sequence of 1A1 variable domains
(CDR domains underlined)

1A1 Heavy Chain Variable Region
EVQLQQSGAELVRSGASVKLSCTASGFNI<u>KDNYMH</u>WVKQRPEQGLEWIG<u>W
                                 CDR1
IDPENGDTEYAPKFQG</u>KATMTADTSSNTAYLQLSSLTSEPAVYYCNT<u>WAY
     CDR2
YGTSYGGFAY</u>WGQGTTVTVSS
     CDR3
(SEQ ID NO: 11)

1A1 Light Chain Variable Region
DIQMTQTPLTLSVTIGQPASISC<u>KSSQSLLDSDGKTYLN</u>WSLQRPGQSPK
                          CDR1
RLIT<u>LVSKLDS</u>GVPDRFTGSGSGTDFTLKISRVEAEDLGVYYC<u>WQGTHFP
    CDR2                                           CDR3
QTF</u>GGGTKLEIK
(SEQ ID NO: 12)

Nucleotide and amino acid comparisons of the 1A1 variable heavy and light chains are also shown in FIG. 8. The sequence of the CDR regions of the 1A1 antibody were determined to be the following:

```
1A1 Heavy Chain Variable Region
CDR1: DNYMH                       (SEQ ID NO: 13)

CDR2: WIDPENGDTEYAPKFQG           (SEQ ID NO: 14)

CDR3: WAYYGTSYGGFAY               (SEQ ID NO: 15)

1A1 Light Chain Variable Region
CDR1: KSSQSLLDSDGKTYLN            (SEQ ID NO: 16)

CDR2: LVSKLDS                     (SEQ ID NO: 17)

CDR3: WQGTHFPQT                   (SEQ ID NO: 18)
```

Example 10

Cloning and Sequencing of mu11K2 Variable Regions

Mouse monoclonal antibody 11K2 was cloned and sequenced according to the following procedure. Total cellular RNA from 11K2 murine hybridoma cells was prepared using the Qiagen RNeasy mini kit according to the manufacturer's recommended protocol.

cDNAs encoding the variable regions of the heavy and light chains were cloned by RT-PCR from total cellular RNA. Following the manufacturers recommended protocols, first-strand cDNAs (prepared with the Amersham First-Strand cDNA Synthesis Kit) were amplified by PCR using the Clontech Advantage 2 PCR Kit. The following primers were used for first-strand synthesis of the 11K2 heavy and light chain cDNAs (Y/T, and R=A/G): 11K2 Heavy Chain cDNA Primer: 5'-AGG TCT AGA AYC TCC ACA CAC AGG RRC CAG TGG ATA GAC-3' (SEQ ID NO:19) and 11K2 Light Chain cDNA Primer: 5'-GCG TCT AGA ACT GGA TGG TGG GAG AM GA-3' (SEQ ID NO:20).

The primers used for PCR amplification of the murine 11K2 immunoglobulin heavy chain variable domain were: 5'-GGG GAT ATC CAC CAT GGR ATG SAG CM KGT MAT SCT CTT-3' (SEQ ID NO:21) and 5' AGO TCT AGA AYC TCC ACA CAC AGG RRC CAG TGG ATA GAC-3' (SEQ ID NO:22) (R=A/G, S=C/G, K=G/T, M=A/C, and Y=C/T). The primers used for PCR amplification of the murine 11K2 immunoglobulin light chain variable domain were: 5'-GAY ATH CAR ATG ACN CAG-3' (SEQ ID NO:23) and 5'-GCG TCT AGA ACT GGA TGG TGG GAG ATG GA-3' (SEQ NO:24) (Y=C/T, H=A/C/T, R=A/G, and N=A/C/G/T).

The PCR was performed at 30 cycles using Clontech's Advantage 2 PCR Kit under the following PCR conditions: denature 0.5 min at 94° C., anneal 1 min at 50° C., and elongate 1 min at 72° C. The PCR products were gel-purified using the Qiagen Qiaquick gel extraction kit following the manufacturer % recommended protocol. Purified 11K2 heavy and light chain PCR products were subcloned into Invitrogen % pCR2.1-TOPO vector using their TOPO TA Cloning kit according to the manufacturer's recommended protocol (pCR-008=11K2 heavy chain, per-033=11K2 light chain. Inserts from multiple independent subclones were sequenced according to methods known in the art and those described in Sanger et al., *PNAS* 74, 5463-5467, incorporated herein by reference, and the subclones were found to be identical.

Sequence data was analyzed according to BLAST analysis (see http://www.ncbi.nlm.nih.gov). Blast analyses of the variable domain sequences confirmed their immunoglobulin identity. The 11K2 heavy chain variable domain was determined to be a member of murine subgroup II(C), while the 11K2 light chain variable region was determined to be a member of murine kappa subgroup V. The predicted amino acid sequences of the mature 11K2 murine variable domains, as well as the determined nucleotide sequences, are shown below in Tables 9 and 10.

TABLE 9

Nucleotide sequence of mu11K2 variable domains

11K2 Heavy Chain Variable Region
```
  1 GAGGTTCAGCTGCAGCAGTCTGGGGCAGAGCTTGTGAAGGCAGGGGCCTCAGTCAAGTTG   60
 Z61 TCCTGCCCAGCTTCTGGCCTCAACATTAAAGACACCTATATGCACTGGGTGAAGCAGAGG  120
 121 CCTGAACAGGGCCTGGAGTGGATTGGAAGGATTGATCCTGCGAATGGTAATACTAAATTT  160
 181 GACCCGAAGTTCCAGGGCAAGGCCACTATAACAGCAGACACATCCTCCAACACAGCCTAC  140
 241 CTGCAGCTCAGCAGCCTGACATCTGAGGACACTGCCGTCTATTACTGTGCTAGAGGCGTC  300
 301 TTTGGCTTTTTTGACTACTGGGGCCAAGGCACCACTCTCACAGTCTCCTCA           351
(SEQ ID NO: 25)
```

11K2 Light Chain Variable Region
```
  1 GACATTCAGATGACTCAGTCTTCATCCTCCTTTTCTGTATCTCTAGGAGACAGAGTCACC   60
 61 ATTACTTGCAAGGCAACTGAGGACATATATAATCGATTAGCCTGGTATCAGCAGAAACCA  120
 121 GGAAGTGCTCCTAGGCTCTTAATTTCTGGTGCAACCAGTTTGGAGACTGGGGTTCCTTCA  180
 181 AGATTCAGTGGCAGTGGATCTGGAAAAGATTACACTCTCAGCATTACCAGTCTTCAGACT  240
 241 GAGGATGTTGCTACTTATTACTGTCAACAGTTTTGGAGTGCTCCGTACACGTTCGGAGGG  300
 301 GGGACCAAGCTGGAGATCAAA                                         321
(SEQ ID NO: 26)
```

TABLE 10

Amino acid sequence of 11K2 variable domains (CDR regions underlined)

11K2 heavy chain variable region
EVQLQQSGAELVKAGASVKLSCPASGLNIK<u>DTYMH</u>WVKQRPEQGLEWIG<u>R
                   CDR1
IDPANGNTKFDPKFQ</u>GKATITADTSSNTAYLQLSSLTSEDTAVYYCAR<u>GV
   CDR2
FGFFDY</u>WGQGTTLTVSS
 CDR3
(SEQ ID NO: 27)

11K2 light chain variable region
DIQMTQSSSSFSVSLGDRVTITC<u>KATEDIYNRLA</u>WYQQKPGSAPRLLIS<u>G
          CDR1
ATSLET</u>GVPSRFSGSGSGKDYTLSITSLQTEDVATYYC<u>QQFWSAPYT</u>FGG
 CDR2                 CDR3
QTKLEIK
(SEQ ID NO: 28)

Nucleotide and amino acid comparisons of the 11K2 variable heavy and light chains are also shown in FIG. 9. The sequence of the CDR regions of the 11K2 antibody were determined to be as follows:

```
11K2 Heavy Chain Variable Region
CDR1: DTYMH                         (SEQ ID NO: 29)

CDR2: RIDPANGNTKFDPKFQG             (SEQ ID NO: 30)

CDR3: GVFGFFDY                      (SEQ ID NO: 31)

11K2 light Chain Variable Region
CDR1: KATEDIYNRLA                   (SEQ ID NO: 32)
```

```
CDR2: GATSLET                       (SEQ ID NO: 33)

CDR3: QQFWSAPYT                     (SEQ ID NO: 34)
```

Based on the results described above, particularly Tables 1 and 3, antibodies were grouped according to their antigen-binding specificity. The CDR region of mAbs which could recognize MCP-1, MCP-2, and MCP-3, including 4N4, 5A13, 6D21, 6I5, 7H1, 11K2, and 1A1 were determined as described above. Sequencing revealed that mAbs 4N4, 5A13, 6D21, 6I5, 7H1, and 11K2 all had identical sequences. Monoclonal antibody 1A1 had a different sequence. Thus, based on CDR cloning, as well as N-terminal sequencing, two distinct pan-MCP monoclonals antibodies were found to exist.

Forming part of the present disclosure is the appended Sequence Listing, the contents of which are summarized in the table below:

TABLE 11

Sequence listing overview

| SEQ ID NO: | Description | Sequence Type |
|---|---|---|
| 1 | MCP-1 MRHAS motif | amino acid |
| 2 | MCP-3 MRHAS motif | amino acid |
| 3 | 1A1 Heavy Chain cDNA Primer | nucleic acid |
| 4 | 1A1 Light Chain cDNA Primer | nucleic acid |
| 5 | 1A1 Heavy Chain cDNA primer | nucleic acid |
| 6 | 1A1 Heavy Chain cDNA primer | nucleic acid |
| 7 | 1A1 Light Chain cDNA primer | nucleic acid |
| 8 | 1A1 Light Chain cDNA primer | nucleic acid |
| 9 | 1A1 Heavy chain variable region | nucleic acid |
| 10 | 1A1 Light chain variable region | nucleic acid |
| 11 | 1A1 Heavy chain variable region | amino acid |
| 12 | 1A1 Light chain variable region | amino acid |
| 13 | 1A1 Heavy Chain Variable Region CDR1 | amino acid |
| 14 | 1A1 Heavy Chain Variable Region CDR2 | amino acid |
| 15 | 1A1 Heavy Chain Variable Region CDR3 | amino acid |
| 16 | 1A1 Light Chain Variable Region CDR1 | amino acid |
| 17 | 1A1 Light Chain Variable Region CDR2 | amino acid |
| 18 | 1A1 Light Chain Variable Region CDR3 | amino acid |
| 19 | 11K2 Heavy Chain cDNA Primer | nucleic acid |
| 20 | 11K2 Light Chain cDNA Primer | nucleic acid |
| 21 | 11K2 Heavy Chain cDNA Primer | nucleic acid |
| 22 | 11K2 Heavy Chain cDNA Primer | nucleic acid |
| 23 | 11K2 Light Chain cDNA Primer | nucleic acid |
| 24 | 11K2 Light Chain cDNA Primer | nucleic acid |

TABLE 11-continued

Sequence listing overview

| SEQ ID NO: | Description | Sequence Type |
|---|---|---|
| 25 | 11K2 Heavy Chain Variable Region | nucleic acid |
| 26 | 11K2 Light Chain Variable Region | nucleic acid |
| 27 | 11K2 heavy chain variable region | amino acid |
| 28 | 11K2 light chain variable region | amino acid |
| 29 | 11K2 Heavy Chain Variable Region CDR1 | amino acid |
| 30 | 11K2 Heavy Chain Variable Region CDR2 | amino acid |
| 31 | 11K2 Heavy Chain Variable Region CDR3 | amino acid |
| 32 | 11K2 Light Chain Variable Region CDR1 | amino acid |
| 33 | 11K2 Light Chain Variable Region CDR2 | amino acid |
| 34 | 11K2 Light Chain Variable Region CDR3 | amino acid |

One of ordinary skill in the art will recognize that many variations and changes may be made to the invention as described in the Detailed Description without departing from the spirit and scope of the invention. The examples provided herein are merely illustrative, and should not be construed as limiting of the scope of the invention, which is set forth in the appended claims. All publications and patent documents cited herein, as well as text appearing in the figures and sequence listing, are hereby incorporated by reference in their entirety for all purposes to the same extent as if each were so individually denoted.

What is claimed is:

1. A method of reducing chemotaxis in a subject suffering from multiple sclerosis comprising administering to the subject an isolated antibody or fragment thereof capable of blocking chemotaxis, wherein said antibody or antigen-binding fragment comprises:
   a) a heavy chain variable region having a CDR1 domain comprising the sequence set forth in SEQ ID NO:29, a CDR2 domain comprising the sequence set forth in SEQ ID NO:30, and a CDR3 domain comprising the sequence set forth in SEQ ID NO: 31; and
   b) a light chain variable region having a CDR1 domain comprising the sequence set forth in SEQ ID NO:32, a CDR2 domain comprising the sequence set forth in SEQ ID NO:33, and a CDR3 domain comprising the sequence set forth in SEQ ID NO:34,
   wherein the isolated antibody is administered in an amount sufficient to reduce the activity of at least one of MCP-1, MCP-2, or MCP-3.

* * * * *

SEQUENCE LISTING

```
<160> NUMBER OF SEQ ID NOS: 34

<210> SEQ ID NO 1
<211> LENGTH: 7
<212> TYPE: PRT
<213> ORGANISM: Homo sapiens

<400> SEQUENCE: 1

Gln Thr Gln Thr Pro Lys Thr
 1               5

<210> SEQ ID NO 2
<211> LENGTH: 7
<212> TYPE: PRT
<213> ORGANISM: Homo sapiens

<400> SEQUENCE: 2

Lys Thr Gln Thr Pro Lys Leu
 1               5

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
aggtctagaa yctccacaca caggrrccag tggatagac                              39

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
gcgtctagaa ctggatggtg ggagatgga                                         29
```

<210> SEQ ID NO 5
<211> LENGTH: 22
<212> TYPE: DNA
<213> ORGANISM: Mus musculus

<400> SEQUENCE: 5
aggtsmarct gcagsagtcw gg                                          22

<210> SEQ ID NO 6
<211> LENGTH: 32
<212> TYPE: DNA
<213> ORGANISM: Mus musculus

<400> SEQUENCE: 6
tgaggagacg gtgaccgtgg tcccttggcc cc                               32

<210> SEQ ID NO 7
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 15
<223> OTHER INFORMATION: n = A, C, G or T

<400> SEQUENCE: 7
gayathcara tgacncag                                               18

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
gcgtctagaa ctggatggtg ggagatgga                                   29

<210> SEQ ID NO 9
<211> LENGTH: 366
<212> TYPE: DNA
<213> ORGANISM: Mus musculus

<400> SEQUENCE: 9
gaggtccagc tgcagcagtc tggggcagaa cttgtgaggt caggggcctc agtcaagttg    60
tcctgcacag cttctggctt caacattaaa gacaactata tgcactgggt gaagcagagg   120
cctgaacagg gcctggagtg gattggatgg attgatcctg agaatggaga tactgaatat   180
gccccgaagt tccagggcaa ggccactatg actgcagaca catcctccaa cacagcctac   240
ctgcagctca gcagcctgac atctgaggac actgccgtct attactgtaa tacatgggct   300
tactacggta ctagctacgg gggatttgct tactggggcc aagggaccac ggtcaccgtc   360
tcctca                                                             366

<210> SEQ ID NO 10
<211> LENGTH: 336
<212> TYPE: DNA
<213> ORGANISM: Mus musculus

<400> SEQUENCE: 10
gatatccaga tgactcagac tccactcact ttgtcggtta ccattggaca accagcctcc    60

```
atctcttgca agtcaagtca gagcctctta gatagtgatg aaagacata tttgaattgg      120 tcgttacaga ggccaggcca gtctccaaag cgcctaatct atctggtgtc taaactggac      180
tctggagtcc ctgacaggtt cactggcagt ggatcaggga cagatttcac actgaaaatc      240
agcagagtgg aggctgagga tttgggagtt tattattgct ggcaaggtac acattttcct      300
cagacgttcg gtggaggcac caagctggag atcaaa                                336
```

```
<210> SEQ ID NO 11
<211> LENGTH: 122
<212> TYPE: PRT
<213> ORGANISM: Mus musculus

<400> SEQUENCE: 11
```

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Asn
            20                  25                  30

Tyr Met His Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Thr Trp Ala Tyr Tyr Gly Thr Ser Tyr Gly Gly Phe Ala Tyr Trp
            100                 105                 110

Gly Gln Gly Thr Thr Val Thr Val Ser Ser
        115                 120

```
<210> SEQ ID NO 12
<211> LENGTH: 112
<212> TYPE: PRT
<213> ORGANISM: Mus musculus

<400> SEQUENCE: 12
```

Asp Ile Gln Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Ser Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

```
<210> SEQ ID NO 13
<211> LENGTH: 5
<212> TYPE: PRT
<213> ORGANISM: Mus musculus

<400> SEQUENCE: 13
```

```
Asp Asn Tyr Met His
1               5

<210> SEQ ID NO 14
<211> LENGTH: 17
<212> TYPE: PRT
<213> ORGANISM: Mus musculus

<400> SEQUENCE: 14

Trp Ile Asp Pro Glu Asn Gly Asp Thr Glu Tyr Ala Pro Lys Phe Gln
1               5                  10                  15

Gly

<210> SEQ ID NO 15
<211> LENGTH: 13
<212> TYPE: PRT
<213> ORGANISM: Mus musculus

<400> SEQUENCE: 15

Trp Ala Tyr Tyr Gly Thr Ser Tyr Gly Gly Phe Ala Tyr
1               5                  10

<210> SEQ ID NO 16
<211> LENGTH: 16
<212> TYPE: PRT
<213> ORGANISM: Mus musculus

<400> SEQUENCE: 16

Lys Ser Ser Gln Ser Leu Leu Asp Ser Asp Gly Lys Thr Tyr Leu Asn
1               5                  10                  15

<210> SEQ ID NO 17
<211> LENGTH: 7
<212> TYPE: PRT
<213> ORGANISM: Mus musculus

<400> SEQUENCE: 17

Leu Val Ser Lys Leu Asp Ser
1               5

<210> SEQ ID NO 18
<211> LENGTH: 9
<212> TYPE: PRT
<213> ORGANISM: Mus musculus

<400> SEQUENCE: 18

Trp Gln Gly Thr His Phe Pro Gln Thr
1               5

<210> SEQ ID NO 19
<211> LENGTH: 39
<212> TYPE: DNA
<213> ORGANISM: Artificial Sequence
<220> FEATURE:
<223> OTHER INFORMATION: primer

<400> SEQUENCE: 19
aggtctagaa yctccacaca caggrrccag tggatagac                              39

<210> SEQ ID NO 20
<211> LENGTH: 29
<212> TYPE: DNA
<213> ORGANISM: Artificial Sequence
<220> FEATURE:
<223> OTHER INFORMATION: primer
```

```
<400> SEQUENCE: 20
gcgtctagaa ctggatggtg ggagatgga                                        29

<210> SEQ ID NO 21
<211> LENGTH: 39
<212> TYPE: DNA
<213> ORGANISM: Artificial Sequence
<220> FEATURE:
<223> OTHER INFORMATION: primer

<400> SEQUENCE: 21
ggggatatcc accatggrat gsagctgkgt matsctctt                             39

<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
aggtctagaa yctccacaca caggrrccag tggatagac                             39

<210> SEQ ID NO 23
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 15
<223> OTHER INFORMATION: n = A,T,C or G

<400> SEQUENCE: 23
gayathcara tgacncag                                                    18

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
gcgtctagaa ctggatggtg ggagatgga                                        29

<210> SEQ ID NO 25
<211> LENGTH: 351
<212> TYPE: DNA
<213> ORGANISM: Mus musculus

<400> SEQUENCE: 25
gaggttcagc tgcagcagtc tggggcagag cttgtgaagg caggggcctc agtcaagttg       60
tcctgcccag cttctggcct caacattaaa gacacctata tgcactgggt gaagcagagg      120
cctgaacagg gcctggagtg gattggaagg attgatcctg cgaatggtaa tactaaattt      180
gacccgaagt tccagggcaa ggccactata acagcagaca catcctccaa cacagcctac      240
ctgcagctca gcagcctgac atctgaggac actgccgtct attactgtgc tagaggcgtc      300
tttggctttt ttgactactg gggccaaggc accactctca cagtctcctc a               351

<210> SEQ ID NO 26
<211> LENGTH: 321
<212> TYPE: DNA
```

<213> ORGANISM: Mus musculus

<400> SEQUENCE: 26

```
gacattcaga tgactcagtc ttcatcctcc ttttctgtat ctctaggaga cagagtcacc      60
attacttgca aggcaactga ggacatatat aatcgattag cctggtatca gcagaaacca     120
ggaagtgctc ctaggctctt aatttctggt gcaaccagtt tggagactgg ggttccttca     180
agattcagtg gcagtggatc tggaaaagat tacactctca gcattaccag tcttcagact     240
gaggatgttg ctacttatta ctgtcaacag ttttggagtg ctccgtacac gttcggaggg     300
gggaccaagc tggagatcaa a                                                321
```

<210> SEQ ID NO 27
<211> LENGTH: 117
<212> TYPE: PRT
<213> ORGANISM: Mus musculus

<400> SEQUENCE: 27

Glu Val Gln Leu Gln Gln Ser Gly Ala Glu Leu Val Lys Ala Gly Ala
1               5                   10                  15

Ser Val Lys Leu Ser Cys Pro Ala Ser Gly Leu Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Val Phe Gly Phe Phe Asp Tyr Trp Gly Gln Gly Thr Thr
            100                 105                 110

Leu Thr Val Ser Ser
        115

<210> SEQ ID NO 28
<211> LENGTH: 107
<212> TYPE: PRT
<213> ORGANISM: Mus musculus

<400> SEQUENCE: 28

Asp Ile Gln Met Thr Gln Ser Ser Ser Phe Ser Val Ser Leu Gly
1               5                   10                  15

Asp Arg Val Thr Ile Thr Cys Lys Ala Thr Glu Asp Ile Tyr Asn Arg
            20                  25                  30

Leu Ala Trp Tyr Gln Gln Lys Pro Gly Ser Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Phe Trp Ser Ala Pro Tyr
                85                  90                  95

Thr Phe Gly Gly Gly Thr Lys Leu Glu Ile Lys
            100                 105

<210> SEQ ID NO 29
<211> LENGTH: 5

```
<212> TYPE: PRT
<213> ORGANISM: Mus musculus

<400> SEQUENCE: 29

Asp Thr Tyr Met His
 1               5

<210> SEQ ID NO 30
<211> LENGTH: 17
<212> TYPE: PRT
<213> ORGANISM: Mus musculus

<400> SEQUENCE: 30

Arg Ile Asp Pro Ala Asn Gly Asn Thr Lys Phe Asp Pro Lys Phe Gln
 1               5                  10                  15

Gly

<210> SEQ ID NO 31
<211> LENGTH: 8
<212> TYPE: PRT
<213> ORGANISM: Mus musculus

<400> SEQUENCE: 31

Gly Val Phe Gly Phe Phe Asp Tyr
 1               5

<210> SEQ ID NO 32
<211> LENGTH: 11
<212> TYPE: PRT
<213> ORGANISM: Mus musculus

<400> SEQUENCE: 32

Lys Ala Thr Glu Asp Ile Tyr Asn Arg Leu Ala
 1               5                  10

<210> SEQ ID NO 33
<211> LENGTH: 7
<212> TYPE: PRT
<213> ORGANISM: Mus musculus

<400> SEQUENCE: 33

Gly Ala Thr Ser Leu Glu Thr
 1               5

<210> SEQ ID NO 34
<211> LENGTH: 9
<212> TYPE: PRT
<213> ORGANISM: Mus musculus

<400> SEQUENCE: 34

Gln Gln Phe Trp Ser Ala Pro Tyr Thr
 1               5
```